(12) United States Patent
Bauer et al.

(10) Patent No.: US 8,697,154 B2
(45) Date of Patent: Apr. 15, 2014

(54) BACTERIAL EXTRACT FOR RESPIRATORY DISORDERS AND PROCESS FOR ITS PREPARATION

(75) Inventors: Jacques Alain Bauer, Saint-Prex (CH); Marco Salvagni, Geneva (CH); Jean-Pierre Leon Vigroox, Bonneville (FR); Laetitia Chalvet, St Genis Pouilly (FR); Carlo Chiavaroli, Thoiry (FR)

(73) Assignee: OM Pharma SA (CH)

( * ) Notice: Subject to any disclaimer, the term of this patent is extended or adjusted under 35 U.S.C. 154(b) by 798 days.

(21) Appl. No.: 12/530,130

(22) PCT Filed: Mar. 5, 2008

(86) PCT No.: PCT/US2008/055906
§ 371 (c)(1),
(2), (4) Date: Mar. 12, 2010

(87) PCT Pub. No.: WO2008/109669
PCT Pub. Date: Sep. 12, 2008

(65) Prior Publication Data
US 2010/0227013 A1    Sep. 9, 2010

Related U.S. Application Data

(60) Provisional application No. 60/904,789, filed on Mar. 5, 2007.

(51) Int. Cl.
*A61K 35/00*    (2006.01)
*A01N 63/02*    (2006.01)
*C12N 1/12*    (2006.01)
*C12N 1/20*    (2006.01)
*C12N 5/00*    (2006.01)
*C12N 5/02*    (2006.01)

(52) U.S. Cl.
USPC ............ 424/780; 435/252.1; 435/252.4; 435/390; 435/822; 435/852; 435/882; 435/885

(58) Field of Classification Search
None
See application file for complete search history.

(56) References Cited

U.S. PATENT DOCUMENTS

| 3,532,790 A | 10/1970 | Greenberg et al. |
| 5,424,287 A | 6/1995 | Bauer et al. |
| 6,248,570 B1 * | 6/2001 | Michon et al. ............... 435/101 |
| 6,264,954 B1 | 7/2001 | Chong et al. |
| 8,236,522 B2 * | 8/2012 | Bauer et al. ................ 435/41 |
| 2001/0051364 A1 | 12/2001 | Michon et al. |
| 2005/0070463 A1 | 3/2005 | Libon et al. |
| 2005/0089968 A1 | 4/2005 | Olivieri et al. |
| 2007/0154492 A1 | 7/2007 | Michon et al. |

FOREIGN PATENT DOCUMENTS

| EP | 269928 | 6/1988 |
| EP | 1368457 A1 | 12/2003 |
| EP | 983342 B1 | 9/2007 |
| EP | 1976857 A2 | 10/2008 |
| EP | 1051506 B1 | 5/2010 |
| EP | 1848448 B1 | 6/2010 |
| GB | 2 021 415 A | 5/1979 |
| WO | 9514026 | 5/1995 |
| WO | WO 98/54296 A1 | 12/1998 |
| WO | WO 99/32653 | 7/1999 |
| WO | WO 02/074939 | 9/2002 |
| WO | 2005017095 | 2/2005 |
| WO | WO 2006/084477 | 8/2006 |
| WO | WO 2007/084856 | 7/2007 |

OTHER PUBLICATIONS

H.C. Birnboim and J. Doly, 1979, "A Rapid Alkaline Extraction Procedure for Screening Recombinant Plasmid DNA", Nucleic Acids Research, vol. 7(6): 1513-1523.

Yue Liu et al., 1997, "Identification of clinical isolates of indole-positive *Klebsiella* spp., including *Klebsiella planticola*, and a genetic and molecular analysis of their beta-lactamases", Journal of Clinical Microbiology, vol. 35(9): 2365-2369.

Pilar Negrete Redondo et al., 2006, "In vitro analysis of the antibacterial activity of *Oedogonium capillare* against pathogenic bacteria in fish", Veterinaria Mexico, vol. 37(2): 209-221 (abstract only).

Philip Domenico et al., 1992, "Rapid plasmid DNA isolation from mucoid gram-negative bacteria", Journal of Clinical Microbiology, vol. 30(11): 2859-2863.

* cited by examiner

*Primary Examiner* — Debbie K Ware
(74) *Attorney, Agent, or Firm* — Law Offices of Albert Wai-Kit Chan, PLLC

(57) ABSTRACT

The present invention relates to an extract from bacterial strains, such as *Staphylococcus*, *Moraxella*, *Klebsiella*, *Streptococcus*, and *Haemophilus*. The extract is useful as a treatment for indications such as respiratory disorders, compositions comprising the extract, and processes of making the extract from media that do not pose a risk of prion diseases.

18 Claims, 10 Drawing Sheets

Parallel

Serpentine

IC50 = 0.0049 mg/ml

CD4 v Foxp3

CD4 v Foxp3

TCR v Foxp3

TCR v Foxp3

BACTERIAL EXTRACT FOR RESPIRATORY DISORDERS AND PROCESS FOR ITS PREPARATION

CROSS REFERENCE TO RELATED APPLICATIONS

This application is a national stage filing under 35 U.S.C. §371 of International Application No. PCT/US08/55906 filed on Mar. 5, 2008. This international application also claims priority to U.S. Provisional Patent Application No. 60/904,789, filed Mar. 5, 2007, the entire disclosure of which is incorporated by reference herein.

DESCRIPTION OF THE INVENTION

1. Field of the Invention

The present invention relates to extracts from bacterial strains useful as a treatment for indications such as respiratory disorders, compositions comprising the extracts, and processes of making the extracts using media that do not pose a risk of prion diseases.

2. Background and Summary of the Invention

The present invention relates to compositions comprising bacterial extracts useful for treating medical conditions such as respiratory disorders. The extracts may comprise bacterial lysates from cultures chosen from the following species:

Moraxella (Branhamella) catarrhalis, Moraxella (Moraxella) catarrhalis, Haemophilus influenzae, Klebsiella pneumoniae, Staphylococcus aureus, Streptococcus pneumoniae, Streptococcus pyogenes, Streptococcus sanguinis, Staphylococcus Hemolyticus, Enterococcus faecalis, Streptococcus mutans, Streptococcus anginosus, Streptococcus mitis, Streptococcus salivarius (aka. Streptococcus viridans), Neisseria sicca, Hemophilus parainfluenzae, Actinobacillus (Hemophilus) actinomycetemcomitans, and Eikenella corrodens.

In some embodiments, the extracts comprise at least one strain from each of the above species of bacteria, while in other embodiments, one or more specific strains from the list above may be removed or substituted with one or more different strains. Some embodiments of the present invention comprise an extract obtained from each of the following bacterial strains: Moraxella (Branhamella) catarrhalis 3622, Moraxella (Branhamella) catarrhalis 3625, Moraxella (Branhamella) catarrhalis I-045, Haemophilus influenzae 8467, Klebsiella pneumoniae ssp. ozaenae 5050, Klebsiella pneumoniae 204, Klebsiella pneumoniae 5056, Staphylococcus aureus I-049, Staphylococcus aureus I-050, Staphylococcus aureus I-051, Staphylococcus aureus I-052, Staphylococcus aureus I-053, Staphylococcus aureus I-054, Streptococcus (Diplococcus) pneumoniae 7465, Streptococcus (Diplococcus) pneumoniae 7466, Streptococcus (Diplococcus) pneumoniae 7978, Streptococcus (Diplococcus) pneumoniae 10319, Streptococcus pyogenes 8191, Streptococcus sanguinis I-046, Streptococcus sanguines I-047, Streptococcus sanguinis I-048, Staphylococcus Hemolyticus 11042, Enterococcus faecalis 103015, Streptococcus mutans 10449, Streptococcus anginosus 10713, Streptococcus mitis 12261, Streptococcus salivarius 102503, Neisseria sicca 103345, Haemophilus parainfluenzae 7857, Actinobacillus (Hemophilus) actinomycetemcomitans 52.105, and Eikenella corrodens 10596. Those strains are deposited according to the Budapest Treaty. The strains indicated in the list with I-number were indexed by the Collection Nationale de Culture des Microorganismes at the Institut Pasteur, 25 rue du Dr. Roux, 75724 Paris, France. All of the other strains were indexed by the National Collection of Type Cultures in London.

In some embodiments, one or more of the specific strains listed above may be omitted, or substituted with a different strain from the same species or from a different species of bacteria. For example, in some embodiments, one or more or even all of strains Staphylococcus Hemolyticus 11042, Enterococcus faecalis 103015, Streptococcus mutans 10449, Streptococcus anginosus 10713, Streptococcus mitis 12261, Streptococcus salivarius 102503, Neisseria sicca 103345, Haemophilus parainfluenzae 7857, Actinobacillus (Hemophilus) actinomycetemcomitans 52.105, and Eikenella corrodens 10596 may be omitted. In other embodiments, one or more Moraxella, Klebsiella, Staphylococcus aureus, Streptococcus pneumoniae, Streptococcus pyogenes, or Streptococcus sanguinis strains may be omitted. Further, to aid digestion, a Lactobacillus strain or another strain of bacteria may also be used.

The extracts may be obtained by a process of alkaline lysis after cells are grown to a suitable optical density in a culture medium. In some embodiments, the bacteria are each grown on a medium that does not pose a risk of prion-related diseases or a risk of other diseases that may be transmitted through ingesting products obtained from animal-based media. For example, in some embodiments a vegetable-based medium is used to grow the cells, such as a soya-based medium. In other embodiments, a synthetic medium is used for cell growth. In yet other embodiments, a medium may include biological extracts such as yeast extract and horse serum, which also do not pose such disease risks.

The lysates may also be filtered to remove nucleic acids and larger cellular debris. In consequence of the filtration, in some embodiments, the amount of nucleic acid present in the extracts is less than 100 µg/mL. In some embodiments, insolubilized compounds such as cell wall debris and insufficiently degraded lipopolysaccharide (LPS) are also removed by the filtration. Hence, in some embodiments, the resulting extract comprises soluble molecular components and does not contain significant amounts of insoluble or particulate material.

Saccharide components may be preserved in the extracts, including lipo-polysaccharide (LPS) components. During the lysis process, saccharides may become chemically modified, for example, cleaved into smaller structures or substituted with other functional groups.

Racemization of amino acids during the lysis process also creates D-amino acids from the naturally occurring L-amino acids found in natural proteins. D-amino acids can be beneficial in increasing bioavailability of the extracts, as proteins constituted principally or partially from D-amino acids are not efficiently digested in the mammalian gut. Thus, antigenic molecules in the extracts that are chemically modified during lysis to contain D-amino acids remain in the patient's body for a longer time, allowing potentially for a stronger immunostimulating action.

While bacterial extracts have been used in the prior art to stimulate the immune system against respiratory diseases, there has been a need to better standardize and control those extracts in order to make them safer, more effective, and longer lasting. For instance, it was previously thought that saccharide components, including potentially toxic lipopolysaccharide (LPS) components should be removed from bacterial extracts for safety reasons. (See, e.g., U.S. Pat. No. 5,424,287.) However, the instant invention provides a process that results in sufficient chemical modifications of LPS components that saccharides be safely retained. Retaining those components may improve efficacy and provide additional antigens to the extracts.

For example, the inventors have discovered that adjusting the pH and the time of lysis may allow for sufficient degradation of potentially allergenic or toxic cell wall components. Prior lysis conditions at lower pH's or shorter times, in contrast, produced extracts in which cell wall components and saccharides were insufficiently chemically modified. (See, e.g., GB 2 021 415 A.) The resulting extracts were too allergenic to be safely administered to patients. In general, the inventors have discovered that products lysed at too low a pH and/or at too short a time had higher toxicity, lower protein extraction, and lower filterability.

The filtration process may also influence the properties of the resulting extract, as the pore size of the filter, and in some cases, the chemical properties of the filter surface, may alter the type of materials that were removed and retained. For example, some embodiments of the instant invention use a filtration process designed to retain saccharides but to remove other molecular components such as nucleic acids.

Thus, the instant invention provides parameters that standardize the bacterial extracts to help maintain consistent safety and efficacy.

BRIEF DESCRIPTION OF THE DRAWINGS

FIGS. 10A and 10C show untreated tissue while FIGS. 10B and 10D show treated tissue.

DETAILED DESCRIPTION OF THE INVENTION

Definitions

Figure 1:
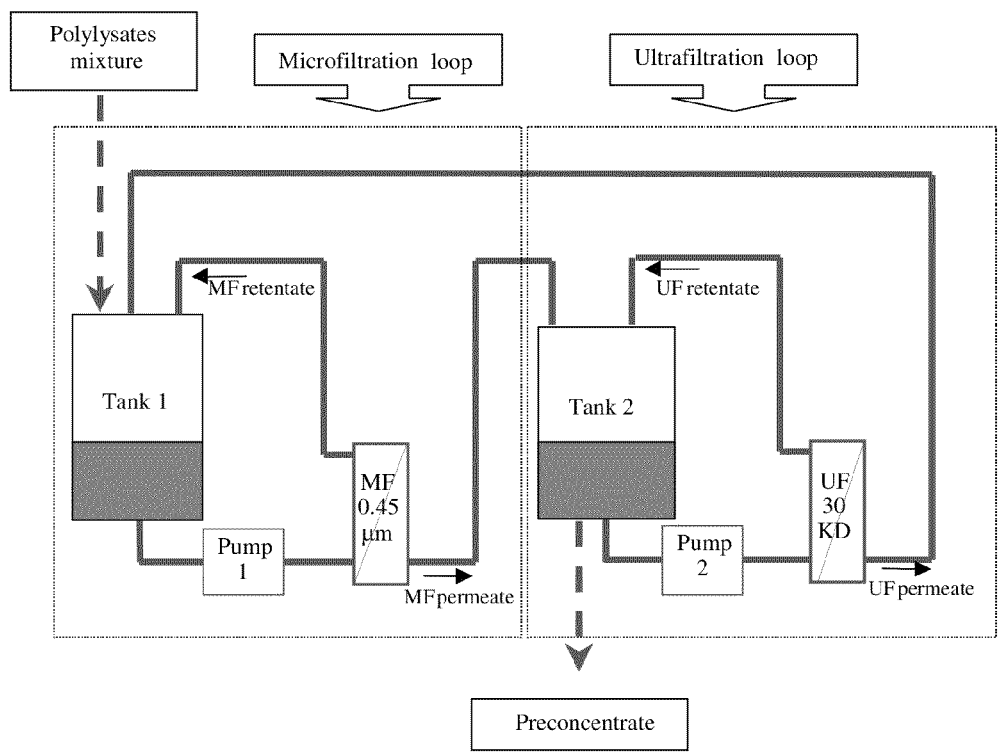
FIG. 1: A diagram of a tangential flow filtration (TFF) system for preparation of bacterial extracts following lysis of bacteria. The diagram shows two different configurations for filters: a parallel mode where all filters work simultaneously and a serpentine mode where filters are configured in a serial mode.
Figure 1:
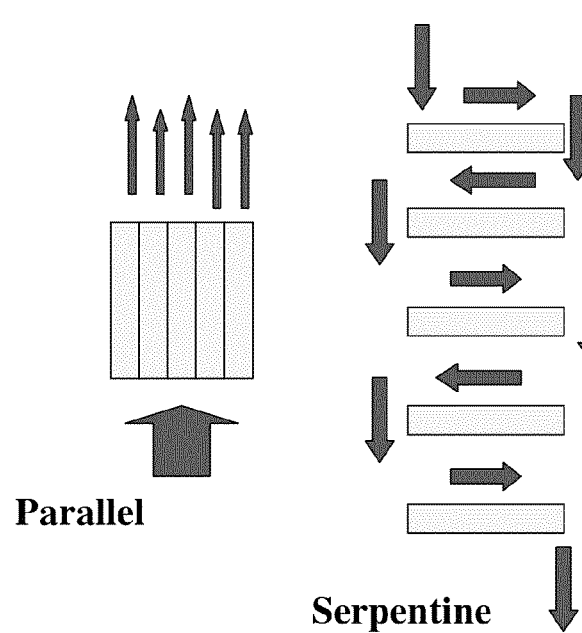
Figure 2A:
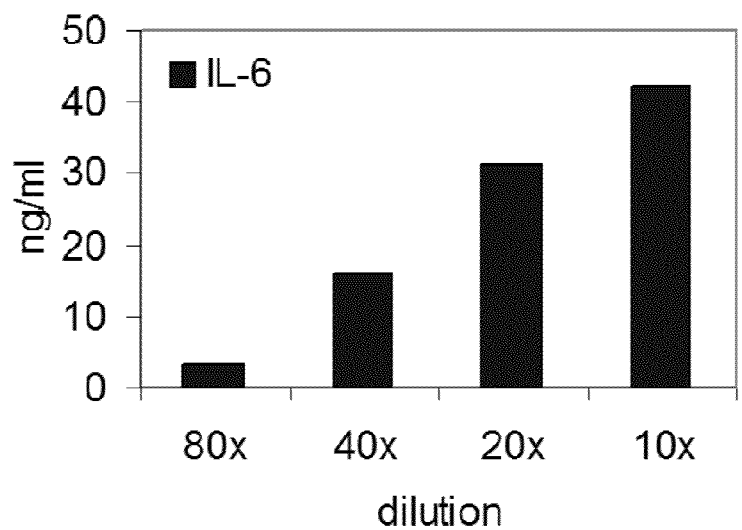
FIGS. 2A-2B: IL-6 and TNF-α production by human PBMC incubated with serial dilutions of a purified mixture of extracts from Examples 2.2, 3.6, 3.7, 3.8, 3.9, and 3.10.
Figure 2B:
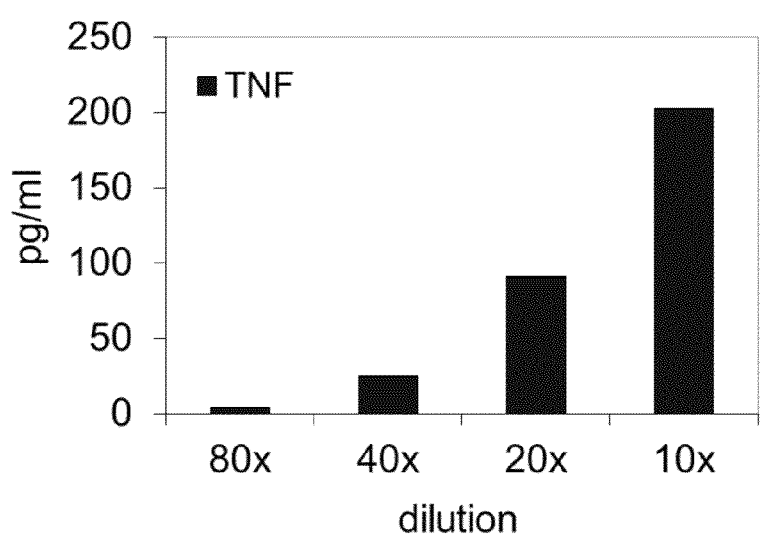

Extract: An extract, as defined herein, means material obtained following lysis of one or more bacterial strains. In some cases, the extract is obtained from only one strain while in others the extract is obtained from a mixture of several different strains.

Alkaline lysis: This is a method of lysing bacterial cells under basic conditions.

Lysate: As used herein, this term means an extract of bacteria obtained from a cell lysis procedure.

Filtration: A filtration process, as described herein, means a passage of an extract or a mixture of extracts, through one or more filters such as microfilters (i.e. microfiltration) or ultrafilters (i.e. ultrafiltration). Such filtration may not necessarily remove 100% of the components it is designed to remove. In some cases, filtration is repeated in several passes or cycles.

Initial pH: That term means the pH measured at the start of a procedure, such as bacterial lysis or filtration.

Saccharides: A saccharide, as defined herein, includes monosaccharides, disaccharides, as well as larger saccharides such as linear and branched polysaccharides. Saccharides also include substituted or chemically modified saccharides, such as lipopolysaccharides (LPS) and their chemically modified variants.

D-amino acids: This term refers to amino acids that exist in dextra-rotatory isomeric forms, as opposed to biosynthetically produced L-amino acids, which exist in levo-rotatory isomeric forms.

Racemization: This term indicates at least partial chemical modification of L-amino acids to D-amino acids.

Medium that avoids the risk of prion-based diseases means a culture medium used at any stage of the preparation of the extracts that does not comprise materials such as serum or meat extracts taken from animals such as cows or sheep, or from any other animal that can transmit prion-based diseases. Examples of such media include vegetable-based or synthetic media and also media using horse serum or media comprising materials taken from animal species that do not transmit prion diseases. Examples of prion-based diseases include, for example, mad cow disease, scrapie, and Creutzfeld-Jacob disease.

A non-animal medium is a medium that does not include components derived from animals. Examples include a vegetable-based (i.e. vegetal) medium, such as a soya medium, and a synthetic medium.

Treatment as used herein means both treatment of current infections, for example, as well as prevention of or protection from the development of new infections, for example.

Subject, as used herein, means any animal subject, including mammalian subjects, such as humans and domestic mammals.

It is understood that the specific bacterial strains identified herein and used in the invention may include the strain obtained from the original deposit recited herein or a genetic clone thereof, including a strain that has been re-deposited at a later time with a different deposit code name, but which is considered to be genetically the same strain as the originally deposited version.

All numbers used herein are approximate, taking into account errors inherent in their measurement, rounding, and significant figures.

Preparation of Extracts

The bacterial extracts of the present invention may be prepared by fermentation followed by heat inactivation and alkaline lysis and filtration. For each strain, to obtain a sufficient amount of material, the fermentation cultures may be started from a working seed lot followed by inoculation into larger fermentation containers.

The media used may be the same for each species. However, supplementary growth factors may be introduced to enhance the growth of some species. In some embodiments, a medium that avoids the risk of prion-based diseases can be used for growing at least some, or all, strains. Examples include non-animal media such as a vegetable-based medium and synthetic media. Other examples include a medium that includes horse serum or another animal extract, taken from a species of animal that does not pose a threat of prion diseases, in contrast to strains grown in the presence of bovine serum or meat extracts which can pose such risks. In some embodiments, an Ala-Gln dipeptide may be added to the medium. The inventors observed that the Ala-Gln dipeptide, in some embodiments, served as a growth stimulator for the bacterial culture.

After fermentation, the resulting biomass from each strain or from a set of strains may be inactivated by a heat treatment, concentrated, and frozen. The cellular material may be lysed with hydroxide ions, such as from NaOH. In some embodiments, a biomass concentration of 2 to 130 g/L of bacterial dry weight may be lysed, such as from 20 to 120 g/L, or from 5 to 90 g/L, or from 10 to 50 g/L, or from 40 to 90 g/L. (The biomass concentration is provided herein as the bacterial dry weight per liter of lysis. The biomass concentration is measured by drying 5 mL of material in a small porcelain dish at 105° C. until it reaches a constant mass and then recording the mass in grams per liter.) For example, Haemophilus strains may be lysed at a biomass concentration of 15-90 g/L, such as from 40 to 90 g/L, such as 40, 50, 60, 70, 80, or 90 g/L or smaller ranges bounded by those concentrations (i.e. 40-50, 70-90, etc.). Streptococcus strains, for instance, may be lysed at 10 to 90 g/L, such as at 10, 20, 30, 40, 50, 60, 70, 80, or 90 g/L or smaller ranges bounded by those concentrations. Moraxella strains may be lysed at, for example, 5 to 60 g/L, or at 10-60 g/L, or at 15-40 g/L, such as at 5, 10, 20, 30, 40, 50, or 60 g/L or smaller ranges bounded by those concentrations; Klebsiella strains may be lysed at, for example, 10 to 50 g/L, such as 25-50 g/L, or 10, 20, 30, 40, or 50 g/L or smaller ranges bounded by those concentrations. Staphylococcus strains may be lysed at, for example, 30 to 90 g/L, such as 30, 40, 50, 60, 70, 80, or 90 g/L or smaller ranges bounded by those concentrations. Neisseria strains may be lysed at, for example, 5 to 60 g/L, such as 5, 10, 20, 30, 40, 50, or 60 g/L or smaller ranges bounded by those concentrations.

In some embodiments, a hydroxide concentration of 0.01 N to 1.2 N may be used for the lysis, such as, from 0.1 to 1 N, or from 0.05 N to 0.4 N, such as 0.05, 0.1, 0.15, 0.2, 0.25, 0.3, 0.35, or 0.4 N, or smaller ranges bounded by those concentrations, or from 0.5 N to 1.0 N, such as 0.5, 0.6, 0.7, 0.8, 0.9, or 1.0 N, or smaller ranges bounded by those concentrations. A base concentration may be used so as to achieve a initial pH of 12 or higher, a pH greater than 12, a pH greater than 12.5, or a pH such as from pH 12.0 to pH 13.4 or pH 12.6 to 13.4. For instance, for Streptococcus strains, the hydroxide concentration may be 0.1-0.7 N, or 0.2-0.5 N, such as 0.2, 0.3, 0.4, or 0.5 N or smaller ranges bounded by those concentrations. For Moraxella or Haemophilus strains, it may be 0.05-0.7 N, or 0.15-0.5 N, such as 0.15, 0.2, 0.25, 0.3, 0.35, 0.4, 0.45, or 0.5 N or smaller ranges bounded by those concentrations. For Klebsiella or Staphylococcus strains, it may be 0.1-0.7 N, or 0.15-0.4 N such as 0.15, 0.2, 0.25, 0.3, 0.35, or 0.4 N or smaller ranges bounded by those concentrations.

The lysis temperature may be from 30 to 60° C., such as from 30-40° C., or from 35-40° C., such as 37° C. The time of lysis may vary from 20 hours or from 40 hours to several days, such as 2, 3, 4, 5, 6, 7, 8, 9, or 10, or even 15 days. For instance, for Haemophilus, Streptococcus, Moraxella, and Staphylococcus strains, a time of 5-9 days may be employed, and a time of 7-10 days for Klebsiella and Neisseria strains. In some embodiments, lysis temperatures of 30-40° C., or 35-40° C., such as 37° C., may be employed for each of the strains and the lysis may occur over a period of 72 to 210 hours (3-9 days), such as 3 days, 4, 5, 6, 7, 8, and 9 days or ranges of hours or days bounded by those times (e.g., 3-4 days, 8-9 days, etc.). It is understood that these ranges of time include any fractional number of days, hours, or minutes, therein.

In some embodiments, when using more than one strain of the same bacterial genus, the strains may be lysed together or separately. The strains may be mixed before or after lysis.

The extracts may be purified by centrifugation and/or filtration. For example, lysates may be centrifuged at 9000× gravity, followed by one or more rounds of filtration on a 0.2 micron filter. In some cases, successive rounds of filtration on larger pore filters followed by filtration on a 0.2 micron filter may be used. Ultrafiltration methods may also be employed in order to help extract soluble materials from the extract, for example, recirculating the ultrafiltration permeate for further microfiltration.

In some embodiments, a tangential flow filtration (TFF) method may be used to filter the extracts and to extract solubilized molecules from larger cellular debris. (See FIG. 1.) (See, e.g., Separations Technology, Pharmaceutical and Biotechnology Applications, Wayne P. Olson, Editor. Interpharm Press, Inc., Buffalo Grove, Ill., U.S.A., p. 126 to 135—ISBN: 0-935184-72-4.) At the beginning of such a process, a diluted bacterial lysate may be stored in a first tank. A microfiltration (MF) loop is started, and the product is pumped. The resulting MF retentate is recycled, while the MF permeate is transferred to a second tank.

After reaching a suitable degree of concentration, an ultrafiltration (UF) loop may be started. The UF permeate may be recirculated back to the first tank for continuous extraction of solubilized compounds from the lysate while the UF retentate is stored in the second tank. During the continuous extraction, the volumes in tanks 1 and 2 may be adjusted by regulation of flow rates of the microfiltration and ultrafiltration permeates.

Several such extraction cycles may be performed, either with TFF or another filtration method. In embodiments that use TFF, at the end of the last cycle, the ultrafiltration loop may be shut down and the microfiltration loop may be run alone and the MF permeate transferred to tank 2.

The microfiltration loop may be fitted with filters of 1.2 microns to 0.1 microns, such as filters of 0.65 to 0.2 microns, or 0.45 microns. The cross-flow may be between 1000 Liters/hours m$^2$ (LHM) and 3000 LHM, such as between 1500 and 2500 LHM, or 2000 LHM with a trans-membrane pressure (TMP) of 0.6 to 2 bars, such as between 0.8 and 1.5 bars, or 1.0 bar. The ultrafiltration loop may be fitted with filters of from 10 KDa to 1000 KDa, such as from 10 KDa to 100 KDa, or from 10 KDa to 30 KDa, or from 30 KDa to 100 KDa. The cross-flow may be between 30 LHM and 1000 LHM, such as between 20 and 500 LHM with a TMP of 0.2 to 1.5 bars, such as between 0.4 and 1.2 bars, or 0.5 bar.

Between 5 and 20 diafiltration volumes may be used to extract solubilized compounds from bacterial cell walls. In some embodiments, between 8 and 15 volumes are used.

Hence, for example, in some embodiments, between 5 and 15 cycles of filtration may be used, in some cases between 8 and 15 cycles, such as 8, 9, 10, 11, 12, 13, 14, or 15 cycles.

Following filtration, the extracts may be further diluted, concentrated or centrifuged, if desired. Purification steps may also be included to remove particulate matter from the extracts. For instance, a further microfiltration using a smaller pore filter may be performed, such as a 0.2 micron filter. After filtration, the yield of solubilized proteins measured by Lowry may be more than 50%, or may be more than 60%, or may be 50 to 90° A), or may be 60-90%, for example. Following filtration, the extract may be lyophilized prior to formulating it for use.

In some embodiments of the invention, a group of lysis conditions may be chosen an applied to one or more bacterial strains. From 40 to 90 g/L, or 40, 50, 60, 70, 80, or 90 g/L of *Haemophilus influenzae* NCTC 8467 may be lysed for 72-200 hours, such as 72, 96, 120, 150, or 200 hours. From 10 to 95 g/L of one or more *Streptococcus* strains, such as 10, 20, 40, 60, 80, 90, or 95 g/L may be lysed for 72-210 hours, such as 72, 96, 120, 150, or 200 hours. From 15 to 80 g/L of one or more *Diplococcus* strains, such as 15, 20, 30, 40, 50, 60, 70, or 80 g/L may be lysed for 72-210 hours, such as 72, 96, 120, 150, or 200 hours. From 10 to 50 g/L of one or more *Klebsiella* strains, such as 10, 15, 20, 25, 30, 35, 40, 45, or 50 g/L may be lysed for 72-210 hours, such as 72, 96, 120, 150, or 200 hours. From 5 to 60 g/L of one or more *Neisseria* strains, such as 5, 10, 15, 20, 25, 30, 35, 40, 45, 50, 55, or 60 g/L may be lysed for 72-210 hours, such as 72, 96, 120, 150, or 200 hours. From 30 to 90 g/L of one or more *Staphilococcus* strains, such as 30, 40, 50, 60, 70, 80, or 90 g/L may be lysed for 72-210 hours, such as 72, 96, 120, 150, 200 hours. In each of those embodiments, the lysis may be conducted at 35-40° C., such as at 37° C. Further, either "moderate" or "strong" lysis conditions may be used for each strain forming the extract or a group of similar strains. As used herein, "moderate" lysis conditions refer to a hydroxide ion concentration of 0.05 to 0.4 N, such as 0.1, 0.2, 0.3, or 0.4 N together with the biomass, time, and temperature parameters given just above for each type of strain (e.g. 35-40° C., 40-90 g/L of biomass and 72-200 hours for *Haemophilus influenzae* NCTC 8467). As used herein, "strong" lysis conditions refer to a hydroxide ion concentration of 0.5 to 1 N, such as 0.5, 0.6, 0.7, 0.8, 0.9 and 1 N, together with the time, temperature, and biomass parameters for each strain given just above. In some embodiments, both strong and moderate lyses may be conducted, with the resulting products mixed together.

In some embodiments of the invention, the extract may be obtained from more than one bacterial strain, such as from at least one gram negative and at least one gram positive strain. Bacterial strains from the same or different species may be mixed before or after lysis. In some embodiments, strains may be mixed, for example, to obtain 1-40% volume of each in the mixture or 15-30% by volume of each genus of bacteria. In some embodiments, the extract may comprise lysis products from, for example, 2, 3, 4, 5 or 10 different genera of bacteria. For instance a mixture of 5 genera may comprise *Haemophilus, Moraxella, Klebsiella, Staphylococcus, Streptococcus* strains, including *Streptococcus sanguinis, pyogenes,* and *pneumoniae*. Some *Streptococcus pneumoniae* strains are also known as, for example, *Diplococcus* strains. In some such 5 genus embodiments, the mixture may contain from 5 to 15% of *Haemophilus* by volume, such as 7-10%, or 7, 8, or 9%; from 5 to 15% of *Diplococcus* by volume, such as 7-10% or 7, 8, or 9%; from 5-20% of *Streptococcus* by volume, such as 7-15%, or 8, 9, 10, 11, or 12%; from 10 to 30% of *Klebsiella* by volume, such as 15-25%, or 16, 17, 18, 19, 20, 21, 22, 23, or 24%; from 10 to 30% of *Staphylococcus* by volume, such as 15-25%, or 16, 17, 18, 19, 20, 21, 22, 23, or 24%; and from 20 to 40% of *Neisseria* by volume, such as 25-35%, or 26, 27, 28, 29, 30, 31, 32, 33, or 34%.

Chemical Properties of Bacterial Extracts

Some embodiments according to the present invention may contain, for example, 5-75 mg/mL of proteins, or 10-65 mg/mL, or 20-45 mg/mL, or 5-40 mg/mL, or 5-20 mg/mL, or 5-10 mg/mL, or 6-8 mg/mL of proteins or a range starting or ending from 5, 6, 8, 10, 15, 20, 25, 30, 35, 40, 45, 50, 55, 60, 65, 70 or 75 mg/mL; 1.5 to 2.5 mg/mL of free amino acids (A.A.), or 1.5 to 2 mg/mL, or 2 to 2.5 mg/mL of free A.A., or a range starting or ending from 1.5, 1.6, 1.7, 1.8, 1.9, 2.0, 2.1, 2.2, 2.3, 2.4, or 2.5 mg/mL of free A.A., calculated from glutamic acid (147.1 g/mol); and 0.3 to 4.5 mg/mL of polysaccharides and monosaccharides, or 0.3 to 4 mg/mL, or 0.4 to 4 mg/mL, or 0.5 to 3.5 mg/mL, or 0.6 to 3 mg/mL or 0.3 to 1 mg/mL or a range starting or ending from 0.3, 0.4, 0.5, 0.6, 0.7, 0.8, 0.9, 1.0, 1.5, 2.0, 2.5, 3.0, 3.5, 4.0, or 4.5 mg/mL of polysaccharides and monosaccharides, such as, e.g. 0.4 to 0.5 mg/mL. For example, some embodiments contain about 6 to 8 mg/mL of proteins, 1.5 to 2.5 mg/mL of free amino acids (A.A.), calculated from glutamic acid (147.1 g/mol) and/or about 0.4 to 0.5 mg/mL of polysaccharides and monosaccharides. Protein concentration is measured by the Lowry assay in accordance with method 2 of European Pharmacopoeia 2.5.33. The sugar concentration is assayed after acid hydrolysis and derivatization according to D. Herbert et al., *Meth. Microbiol.* 5B: 266 et seq. (1971). The glutamate (glutamic acid) concentration is measured by converting amino acids to isoindole derivatives and measuring absorbance at 340 nm, according to Roth M., Fluorescence reaction for amino acids, *Anal. Chem.,* 43, 880-882, (1971).

In some embodiments, the concentration of LPS equivalents based on a limulus amoebocyte lysate (LAL) chromogenic test is less than 1000 ng/ml, or less than 500 ng/ml, less than 200 ng/ml, or less than 100 ng/ml.

Lysis of bacteria according to the present invention may result in partial hydrolysis of proteins as well as deamination, deamidation, and partial racemization of amino acids from L to D. In one analytical study of an extract according to the invention, peaks representing D-aspartic acid, D-glutamic acid, D-serine, D-methionine, D-histidine, D-alanine, D-arginine, D-phenylalanine, D-tyrosine, D-leucine, and D-lysine were each observed. The percentage of D-amino acids of those species in that study ranged from 3% to 40%. Hence, some embodiments of the invention allow for racemization of one or more of serine, threonine, histidine, alanine, arginine, tyrosine, phenylalanine, leucine, and lysine, such as all of the above amino acids, or any selection of more than one but less than all of the above amino acids, such as, for example, alanine, phenylalanine and lysine. In some embodiments, at least 10% of one or more of the above amino acids may become racemized from D to L. In other embodiments, at least 40% of one or more of the above amino acids may become racemized.

Lysis of bacteria according to the present invention may result in a diminution of the molecular weight of component molecules from 0 to 300 kDa to 0 to 100 kDa, or 0 to 60 kDa due to hydrolysis.

Biological Activities of Bacterial Extracts

Extracts according to the invention may be effective to treat patients suffering from or at risk of developing medical conditions such as respiratory disorders and allergic reactions or conditions. Extracts according to the invention may be effective to treat, for example, upper and lower respiratory infections, atopic dermatitis, nasopharyngitis, sinusitis, pharyngitis, tonsillitis, laryngitis, tracheitis, laryngopharyngitis, influenza, pneumonia, bronchopneumonia, bronchitis, lower respiratory infections, allergic rhinitis, allergic asthma, rhinitis, nasopharyngitis, pharyngitis, sinusitis, tonsillitis, laryngitis, laryngotracheitis, bronchitis, obstructive pulmonary disease with acute lower respiratory infection, and obstructive pulmonary disease with acute exacerbation.

Biological activity of extracts may be determined by several assays. For example, a peripheral blood mononuclear cell (PBMC) assay tests the production of the cytokine IL-6 from PBMC's and can screen for the ability of an extract to stimulate the immune system. For example, in some embodiments, the in vitro IL-6 concentration measured in supernatants of PBMCs stimulated with the extracts of the invention ranged from 2000 pg/ml to 70,000 pg/ml, 2000 pg/ml to 50,000 pg/ml, 2000 pg/ml to 30,000 pg/ml, 2000 pg/ml to 20,000 pg/ml, 2000 pg/ml to 10,000 pg/ml, or 5000 pg/ml to 70,000 pg/ml, 5000 pg/ml to 50,000 pg/ml, 5000 pg/ml to 30,000 pg/ml, 5000 pg/ml to 25,000 pg/ml, or 5000 pg/ml to 10,000 pg/ml, or 15,000 pg/ml to 25,000 pg/ml. When LPS was used as an agonist control (at 0.01 µg/ml), the values obtained ranged, depending from the donors, from 5,000 pg/ml to 70,000 pg/ml.

A murine nitric oxide (NO) test measures production of NO by murine macrophages, which also indicates immune stimulation. For example, macrophages produce NO in order to kill invading bacteria. In some embodiments, in vitro nitrous oxide (NO) activity for embodiments of the present invention tested at concentrations ranging from 0.001 mg/ml to 10 mg/ml of soluble dry weight provided maximal responses ranging from 3 µM to 100 µM nitric oxide, or 3 µM to 90 µM, 3 µM to 80 µM, 3 µM to 70 µM, 3 µM to 60 µM, 3 µM to 50 µM, 3 µM to 40 µM, 3 µM to 30 µM, 3 µM to 20 µM, 3 µM to 10 µM, or 5 µM to 80 µM, 5 µM to 60 µM, 5 µM to 40 µM, 5 µM to 20 µM, or 10 µM to 80 µM, 10 µM to 70 µM, 10 µM to 50 µM, 10 to 30 µM, or 10 µM to 15 µM, or ranges beginning or ending from 3, 5, 10, 15, 20, 25, 30, 35, 40, 45, 50, 55, 60, 65, 70, 75, 80, 85, 90, 95, or 100 µM.

Activities observed on human peripheral blood mononuclear cells and murine macrophages in vitro may depend on variables such as the amount of bacterial dry weight biomass to be lysed, i.e. the "starting material" for lysis, the duration of the alkaline lysis, and the initial percentage of NaOH or initial pH used in the lysis.

Combination of in vitro activity tests such as PBMC and NO with determination of LPS concentration such as by LAL also may provide information concerning the balance of activity vs. toxicity risk for a given bacterial extract.

The extracts of this invention may also be active against aerosol influenza virus infection, such as against A/PR/8/34 (H1N1) infection. In one study, for example, an extract according to the present invention was able to confer complete immunoprotection in mice at a dose of 10 mg/mouse, as judged by mortality, lung virus titration, clinical symptoms, and antibody titers. In contrast, only 70% of control animals survived infection.

As another example, the survival rate 13 days after challenge of at least 8 mice having wild-type LPS sensitivity with *Salmonella thyphimurium*, is at least 60% when those mice are first treated for 10 days with effective amounts of some embodiments of the present invention. The dose of *Salmonella thyphimurium* for the challenge may be chosen such that untreated mice or mice treated with a water or blank formulation control containing excipients but no extract have a survival rate of 60% or less, such as 50% or less. In some cases, the survival rate for the extract-treated mice is at least 70%, at least 80%, at least 80%, at least 90%, or at least 95%.

Furthermore, embodiments of this invention may also inhibit the secretion of histamine by compound 48/80-stimulated mast cells to a statistically significant degree, as shown in detail further below. For example, embodiments of the invention may exhibit an IC-50 value in a compound 48/80-stimulated mast cell assay of, for example, between 0.0005 and 0.01 mg/mL, such as between 0.0005 and 0.005 mg/mL, or between 0.001 and 0.01 mg/mL, or between 0.002 and 0.008 mg/mL, or between 0.004 and 0.006 mg/mL, for example.

Compositions Comprising the Bacterial Extracts

The lyophilized extract mixture may be formulated in a number of different ways for eventual administration. For example, oral tablets, capsules, pills, may be prepared, as well as liquid formulations or aerosols. Formulations for infusion or injection may also be prepared. Embodiments of this invention can be formulated, for example, as solid dosage forms or liquid dosage forms. Exemplary solid dosage forms may include, for example, a tablet, e.g. coated tablet, chewable tablet, effervescent tablet, sublingual tablet, granulates, powder, or a capsule) containing the extract, and optionally, one or more nutritional and/or dietary supplements. Solid dosage forms may also contain diluents, fillers, and/or other excipients. Other excipient components may be added such as preservatives, colorants, flavourings, and sweeteners. It is also possible to prepare powder or granulate formulations. Liquid dosage forms as solutions, syrups, suspensions, or drops can also be utilized for the oral route.

WORKING EXAMPLES

Example 1

Bacterial Cultures

Example 1.1

Culture of *Haemophilus Influenzae* NCTC 8467
Initial Culture Conditions

Culture media was prepared by dissolving in purified water the following components: Sodium chloride: 3 g/L; Sodium monohydrogen phosphate: 2 g/L; Sodium acetate: 0.5 g/L; Soya peptone 40 g/L; Glucose: 6 g/L; Inosine: 0.1 g/L; Calcium chloride: 0.02 g/L; Potassium chloride: 0.1 g/L; Sodium bicarbonate: 0.6 g/L; Sodium pyruvate: 0.06 g/L; Metal solution (copper sulfate: 3 mg/l; iron chloride: 830 mg/l; zinc sulfate: 860 mg/l; sulfuric acid: 1.1 mg/L): 0.5 mL/L; Hemin: 25 mg/l; NADH (β-nicotinamide adenine dinucleotide disodium salt reduced trihydrate) 25 mg/l. After dissolution, the pH was adjusted to 7.2. After sterilizing the media, small Erlenmeyer flasks were individually inoculated with the content of frozen vials (containing 1.5 mL of frozen bacteria) and incubated at 37° C. for 8 hours. Then aliquots of this culture were transferred to larger Erlenmeyer flasks containing 150 mL of culture media, and incubated again in the same conditions. Another fermentation step with 1000 mL of culture media was performed in the same conditions but with 50 mg/L of hemin and 50 mg/L of NADH added before inoculation (OD at 700 nm for the 10 ml culture 1 after 10 hours: 3.7, for the 1000 ml culture after 11 hours: 13.5.). Then, the entire 1000 ml culture contents was transferred to prefermenters.

Culture Conditions in Prefermenters

Culture media was prepared by dissolving in purified water the following components: Sodium chloride: 3 g/L; Sodium monohydrogen phosphate 2 g/L; Sodium acetate: 0.5 g/L;

Soya peptone 40 g/L; Glucose 6 g/L; Inosine 0.1 g/L; Calcium chloride 0.02 g/L; Potassium chloride 0.1 g/L; Sodium bicarbonate 0.6 g/l; Sodium pyruvate 0.06 g/l; Metal solution: 0.5 mL/L; Hemin: 1 mg/L; NADH: 10 mg/L, Polypropylene glycol: 0.06-0.10, mL/L. The incubation temperature was regulated at 30° C., with stirring and aeration. The pH was not regulated during the culture. After 13 hours, 2 prefermenters were transferred to a fermenter (OD at 700 nm culture 1 after 6 hours: 1.53; culture 2 after 8.5 hours: 1.90). The cultures of the prefermenters were transferred under sterile conditions into fermenters.

Culture Conditions in Fermenters

Culture media was prepared by dissolving in purified water the following components: Sodium chloride: 3 g/l, Sodium monohydrogen phosphate: 2 g/L; Sodium acetate 0.5 g/L, Soya peptone 40 g/L; Inosine 0.1 g/L; Calcium chloride 0.02 g/L; Potassium chloride 0.1 g/L, Sodium bicarbonate 0.6 g/L; Sodium pyruvate: 0.06 g/L; Metal solution: 0.5 mL/L; Hemin 1.5 mg/l; NADH: 15 mg/l; Polypropylene glycol: 0.02-0.04 mL/L.

After sterilization, 15 g/L glucose was added to the culture. The incubation temperature was regulated at 35° C., with stirring and aeration. The pH was regulated at 6.8 during the culture. After 8 hours, the cultures (OD at 700 nm, culture 1 after 7.25 hours: 3.69; culture 2 after 8.75 hours: 3.55) were inactivated by heat treatment at 90 to 100° C. and transferred to a harvest Tank. Once inactivated, the cultures were transferred to a centrifuge in order to separate the biomass from the culture medium and concentrate. Harvested biomass was stored in a tank connected to a centrifuge. The retentate of centrifuge (1000 l/h) was recycled to a storage tank whereas the permeate was evacuated. The biomass was concentrated and then harvested in a sterile tank. After 3.25 hours, 31,768 g of biomass were harvested. OD of the concentrated biomass was 237.4 at 700 nm. The biomass was divided into a series of aliquots containing 425 g of dry weight biomass. The aliquots were then frozen at −15° C.

Example 1.2

*Staphylococcus* Cultures

Culture Conditions in Erlenmeyer flasks

Culture media for *Staphylococcus aureus* 049 (StAu 049), *Staphylococcus aureus* I-050 (StAu 050), *Staphylococcus aureus* I-051 (StAu 051), *Staphylococcus aureus* I-052 (StAu 052), *Staphylococcus aureus* I-053 (StAu 053) and *Staphylococcus aureus* I-054 (StAu 054) was prepared by dissolving in purified water the following components: Sodium chloride 2 g/L; Sodium monohydrogen phosphate 2 g/L; Sodium acetate 0.5 g/L; Soya peptone 40 g/L; Glucose 6 g/L. Then 0.012 L of media was inoculated with 1.5 mL of frozen bacteria. The culture was incubated at 37° C. for 7 hours under stirring at 180 rpm and pH 6.9. Successive culture steps from 12 to 1000 mL were performed.

Culture Conditions in Prefermenters

The same media as the preceding step was prepared for prefermenters, but with addition of polypropylene glycol 0.06-0.10 mL/L. Media was sterilized in situ at 123° C. for 30 min. 1000 ml of culture from the previous step was transferred into prefermenters with stirring and aeration. The incubation temperature was regulated at 37±2° C. The pH was not regulated during the culture. After 6 hours, the 2 prefermenters were transferred to fermenters.

Culture in Fermenters

Culture media for StAu 049 was prepared by dissolving in purified water the following components: Sodium chloride 2 g/L; Sodium monohydrogen phosphate 2 g/L; Sodium acetate 0.5 g/L; Soya peptone 40 g/L; Polypropylene glycol 0.04 mL/L. The media was sterilized in situ. Glucose (14 g/L) was added to the culture. The incubation temperature was regulated at 37° C. with stirring and aeration. The pH was regulated at 6.4±0.5. After 7 hours, the cultures were inactivated by heat treatment at 90 to 100° C. and transferred to a harvest tank. The biomass was then separated from the culture media by centrifugation. The biomass was divided into a series of aliquots containing a certain amount of dry weight biomass.

The biomass dry weight in each aliquot was: StAu 049: 327 g, StAu 050: 297 g, StAu 051: 375 g, StAu 052: 363 g, StAu 053: 446 g and StAu 054: 365 g.

Example 1.3

*Klebsiella* Cultures

Initial Culture Conditions

Culture media for *Klebsiella pneumoniae* NCTC 5050 (Klba 5050), *Klebsiella pneumoniae* NCTC 5056 (Klba 5056) and *Klebsiella pneumoniae* NCTC 204 (Klba 204) was prepared by dissolving in purified water the following components: Sodium chloride 2 g/L; Sodium monohydrogen phosphate 2 g/L; Sodium acetate 0.5 g/L; Soya peptone 40 g/L; Glucose 6 g/L. Then 0.012 L of media was inoculated with 1.5 mL of frozen bacteria. The culture was incubated at 37° C. for 10 hours with stirring and an initial pH set at 6.9. Successive culture steps from 0.012 to 1.0 Liters were performed.

Culture Conditions for Klba 5050 in Prefermenters

The same media as the previous step was prepared for prefermenters, but with addition of polypropylene glycol 0.06 mL/L. One liter of culture from the previous step was transferred to prefermenters. The incubation temperature was regulated at 37° C. with stirring and aeration. The pH was not regulated during the culture. After 6 hours, the two prefermenters were transferred to a fermenter.

Culture Conditions in Fermenters

Culture media for Klba 5050 was prepared by dissolving in purified water the following components: Sodium chloride 2 g/L; Sodium monohydrogen phosphate 2 g/L; Sodium acetate 0.5 g/L; Soya peptone 40 g/L and polypropylene glycol 0.02 mL/L. The media was sterilized in situ and 21 g/L glucose was added. The incubation temperature was regulated at 37° C. with stirring and aeration. The pH was regulated at 6.6 during the culture. After 8 hours, the cultures were inactivated by heat treatment at 90 to 100° C. and transferred to a harvest tank. The biomass was then separated from the culture media by centrifugation. Biomass dry weight in each aliquot was: Klba 5050: 393 g, Klba 5056: 455 g and Klba 204: 440 g.

Example 1.4

*Moraxella catarrhalis* Cultures

Initial Culture Conditions

Culture media for *Moraxella catarrhalis* NCTC 3622 (NeCa 3622); *Moraxella catarrhalis* NCTC 3625 (NeCa 3625) and *Moraxella catarrhalis* 1-045 (NeCa 045) was prepared by dissolving in purified water the following components: Sodium chloride: 3 g/L; Sodium monohydrogen phosphate: 2 g/L; Sodium acetate: 0.5 g/L; Soya peptone: 40 g/L; Starch: 0.1 g/L; Inosine: 0.1 g/L; Calcium Chloride: 0.02 g/L; Potassium Chloride: 0.1 g/L; Sodium bicarbonate: 0.6 g/L; Sodium pyruvate: 0.06 g/L; Metal solution: 0.5 mL/L (Metal Solution composition: Copper Sulfate 3 mg/L; iron Chloride: 830 mg/L; zinc sulfate: 860 mg/L; sulfuic acid: 1.1 mg/L);

Dipeptide ALA-GLN (200 mg/mL in 0.9% NaCl Solution): 10 mg/L (for first culture step 50 mg/L; for 1 Liter culture step 10 mg/L). Then 0.012 L of media was inoculated with 1.5 mL of frozen bacteria. The culture was incubated at 37° C. for 10 hours with stirring. The initial pH was set at 7.2. Successive culture steps from 0.012 to 1.0 L were performed in the same conditions.

Culture in Prefermenters

The same media as the previous step was prepared for prefermenters, but with addition of polypropylene glycol 0.06-0.10 mL/L and concentration of ALA-GLN adjusted to 4 mg/L. Media was sterilized in situ. One liter of culture from the previous step was transferred to prefermenters. The incubation temperature was regulated at 33° C. with stirring and aeration. The pH was not regulated during the culture. After 10 hours, the 2 prefermenters were transferred to fermenters.

Culture Conditions in Fermenters

The same media as the Erlernmeyer step was prepared for prefermenters, but with addition of polypropylene glycol 0.06 mL/L and without ALA-GLN or glucose. The incubation temperature was regulated at 33° C. with stirring and aeration. The pH was not regulated during the culture. After 10.5 hours, the cultures were inactivated by heat treatment at 90 to 100° C. and transferred to a harvest tank. The biomass was then separated from the culture media by centrifugation. The biomass dry weight in each aliquot was: NeCa 3622: 361 g, NeCa 3625: 351 g and NeCa 045: 223 g.

Example 1.5

*Streptococcus* Cultures

Initial Culture Conditions

Culture media for *Streptococcus pneumoniae* NCTC 7465 (StPn 7465), *Streptococcus pneumoniae* NCTC 7466 (StPn 7466), *Streptococcus pneumoniae* NCTC 7978 (StPn 7978), *Streptococcus pneumoniae* NCTC 10319 (StPn 710319), *Streptococcus sanguinis* I-046 (StSa 046), *Streptococcus sanguinis* I-047 (StSa 047), *Streptococcus sanguinis* I-048 (StSa 048) and *Streptococcus Pyogenes* NCTC 8191 (StPy 8191) was prepared by dissolving in purified water the following components: Sodium chloride: 2 g/L; Sodium monohydrogen phosphate: 2 g/L; Sodium acetate: 0.5 g/L; Soya peptone: 40 g/L; Glucose: 6 g/L; Horse Serum: 50 mL/L. After sterilisation, 0.012 L of media was inoculated with 1.5 mL of frozen bacteria. The culture was incubated at 37° C. for 14 hours with stirring. Then, 10 mL of this culture was transferred to flasks containing 150 mL of culture media and incubated again in the same conditions for 10 hours. A final step was performed under the same conditions in a larger flask containing 1000 mL of culture media with 20 mL/L Horse Serum before being added to the prefermenter.

Culture in Prefermenters

The same media as the previous step was prepared for prefermenters, with addition of polypropylene glycol 0.06 mL/L and a concentration of Horse Serum of 8 mL/L. One liter of the previous culture was transferred to two prefermenters. The incubation temperature was regulated at 30° C. with stirring. The pH was not regulated during the culture. After 14 hours, the 2 prefermenters were transferred to a fermenter.

Culture in Fermenters

The same media as the Erlernmeyer step was prepared for prefermenters, but with addition of polypropylene glycol 0.06 mL/L and a Horse Serum concentration of 1.2 mL/L. 15.75 kg of glucose was added during the culture. The incubation temperature was regulated at 37° C. with stirring. The pH was regulated at 6.4 with concentrated KOH. After 9.25 hours, the cultures were inactivated by heat treatment at 90 to 100° C. and transferred to a harvest tank. The biomass was then separated from the culture media by centrifugation. StSa 046, StSa 047, StSa 048 and StPy 8191 were aerated with sterile air and did not need addition of Horse serum for the culture. The biomass dry weight in each aliquot was: StPn 7465: 134 g, StPn 7466: 142 g StPn 7978: 134 g StPn 10319: 153 g StSa 046: 246 g, StSa 047: 232 g, StSa 048: 353 g and StPy 8191: 269 g.

Example 2

Bacterial Lysis

HAIN 8467 Example 2.1

Aliquots of HaIn 8467 from Fermentation Example 1.1 of Bacterial biomass were thawed at room temperature and diluted with a saline solution (8 g/L NaCl) to reach 79 g/L dry weight. Alkalinization at 0.2 M NaOH was performed. The lysis was incubated for 120 hours at 35-40° C. under continuous stirring. During the lysis, the pH was monitored so as not to decrease by more than 0.5 pH units. Results. 82.2 mg/mL of solubilized dry weight (SOW) and 32.4 mg/mL of proteins (Prot) and 6.2 mg/mL of total amino acids (A.A) calculate in glutamic acid (147.1 g/mol), measured by OPA, 2.40 mg/mL of reducing sugars measured by OPA (Carbohydrates).

Protein concentration (Prot) was measured by a Lowry assay (see European Pharmacopoeia 2.5.33, under "total protein—method 2"). The total free amino acid concentration (A.A) was measured by converting amino acids to isoindole derivatives and measuring absorbance at 340 nm, according to Roth M., Fluorescence reaction for amino acids, *Anal. Chem.*, 43, 880-882, (1971). Results are expressed in equivalents of glutamic acid. The sugar (Carbohydrates) concentration was assayed after acid hydrolysis and derivatization according to D. Herbert et al., *Meth. Microbiol.* 5B: 266 et seq. (1971).

HAIN 8467 Example 2.2

Biomass according to Example 1.1 was diluted to 58.2 g/L. Alkalinization at 0.2 M NaOH was performed. The lysis was incubated for 5 days at 35-40° C. under continuous stirring. (Soluble Dry Weight (SDW): 70.0 mg/ml; Lowry Protein (Prot): 30.0 mg/ml; Amino Acids (A.A): 6.0 mg/ml; Carbohydrates: 2.60 mg/ml.) NOx production in mg of active dry weight/mL, 0.02 mg/mL (C1), 0.2 mg/mL (C2), and 2.0 mg/mL (C3): C1: 18.7 µM, C2: 20.8 µM, C3: 12.1 µM.

HAIN 8467 Example 2.3

Biomass according to Example 1.1 was diluted to 20 g/L. Alkalinization at 0.045 M NaOH was performed. The lysis was incubated for 5 days at 35-40° C. under continuous stirring. (SDW: 29.99 mg/ml. Prot: 4.8 mg/ml; Carbohydrates: 0.2 mg/ml.)

HAIN 8467 Example 2.4 (OP0662L)

Biomass according to Example 1.1 was diluted to 12.5 g/L. Alkalinization at 0.05 M NaOH was performed. The lysis was incubated for 2 days at 35-40° C. under continuous stirring.

(SDW: 11.2 mg/ml; Prot: <0.2 mg/ml; A.A: 2.0 mg/ml; Carbohydrates: 0.4 mg/ml.). D-amino acid percentage: 15% D-Ala, 9% D-Leu, 45% D-Ser, 21% D-Asx, 15% D-Met, 11% D-Phe, 9% D-Glx.

HAIN 8467 Example 2.5

Biomass according to Example 1.1 was diluted to 127 g/L. Alkalinization at 0.7 M NaOH was performed. The lysis was incubated for 2 days at 35-40° C. under continuous stirring. (SDW: 157.2 mg/ml; Prot: 86 mg/ml; A.A: 20.0 mg/ml; Carbohydrates: 4.0 mg/ml.) D-amino acid percentage: 22% D-Ala, 11% D-Leu, 54% D-Ser, 41% D-Asx, 35% D-Met, 32% D-Phe, 29% D-Glx, 6% D-Tyr. NOx production in mg of active dry weight/mL, 0.02 mg/mL (C1), 0.2 mg/mL (C2), and 2.0 mg/mL (C3): C1: 9.1 µM, C2: 18.5 µM, C3: 3.1 µM.

HAIN 8467 Example 2.6

Biomass according to Example 1.1 was diluted to 12.5 g/L. Alkalinization at 0.05 M NaOH was performed. The lysis was incubated for 3 days at 35-40° C. under continuous stirring. (SDW: 10.8 mg/ml; Prot: less than 0.5 mg/ml; A.A: 2.0 mg/ml; Carbohydrates: 0.4 mg/ml) D-amino acid percentage: 10% D-Ala, 9% D-Leu, 56% D-Ser, 22% D-Asx, 16% D-Met, 13% D-Phe, 11% D-Glx. NOx production in mg of active dry weight/mL, 0.02 mg/mL (C1), 0.2 mg/mL (C2), and 2.0 mg/mL (C3): C1: 20.2 µM, C2: 26.7 µM, C3: 4.3 µM.

HAIN 8467 Example 2.7

Biomass according to Example 1.1 was diluted to 127 g/L. Alkalinization at 0.7 M NaOH was performed. The lysis was incubated for 3 days at 35-40° C. under continuous stirring. (SDW: 168.8 mg/ml; Prot: 90 mg/ml; A.A: 22 mg/ml; Carbohydrates: 4.2 mg/ml) D-amino acid percentage: 36% D-Ala, 8% D-Leu, 9% D-Ser, 44% D-Asx, 42% D-Met, 37% D-Phe, 37% D-Glx, 37% D-Tyr.

HAIN 8467 Example 2.8

Biomass according to Example 1.1 was diluted to 12.5 g/L. Alkalinization at 0.7 M NaOH was performed. The lysis was incubated for 10 days at 35-40° C. under continuous stirring. (SDW: 47.2 mg/ml; Prot: less than 0.2 mg/ml; A.A: 4.0 mg/ml; Carbohydrates: 0.2 mg/ml) D-amino acid percentage: 3% D-Ala, 13% D-Leu, 54% D-Ser, 45% D-Asx, 43% D-Met, 42% D-Phe, 41% D-Glx. NOx production in mg of active dry weight/mL, 0.02 mg/mL (C1), 0.2 mg/mL (C2), and 2.0 mg/mL (C3): C1: 7.5 µM, C2: 16.0 µM, C3: 8.6 µM.

HAIN 8467 Example 2.9

Biomass according to Example 1.1 was diluted to 127 g/L. Alkalinization at 0.05 M NaOH was performed. The lysis was incubated for 196 hours at 35-40° C. under continuous stirring. D-amino acid percentage: 14% D-Ala, 5% D-Asx, 11% D-Met, 5% D-Glx.

STPY 8191 Example 2.10

One aliquot of StPy 8191 from Example 1.5, containing 269 g of bacterial material was thawed at room temperature and was diluted with a saline solution (8 g/L NaCl) to reach 59.8 g/L dry weight. Alkalinization at 0.2 M NaOH was performed. Then, the lysis was incubated for 192 hours at 35-40° C. under continuous stirring. During the lysis, the pH was monitored so as not to decrease by more than 0.5 pH units. (SDW: 61.92 mg/mL, Prot: 31.68 mg/mL; A.A.: 7.2 mg/mL; Carbohydrates: 7.2 mg/mL). D-amino acid percentage: 22% D-Ala, 11% D-Leu, 54% D-Ser, 41% D-Asx, 35% D-Met, 32% D-Phe, 29% D-Glx, 6% D-Tyr. NOx production in mg of active dry weight/mL, 0.02 mg/mL (C1), 0.2 mg/mL (C2), and 2.0 mg/mL (C3): C1: 4.9 µM, C2: 11.8 µM, C3: 6.7 µM.

STSA 046 Example 2.11

Biomass according to Example 1.5 was diluted to 30 g/L. Alkalinization at 0.022 N NaOH was performed. The lysis was incubated for 8 days at 35-40° C. under continuous stirring.

STPY 8191 Example 2.12

Biomass according to Example 1.5 was diluted to 100 g/L. Alkalinization at 0.7 M NaOH was performed. The lysis was incubated for 2 days at 35-40° C. under continuous stirring. (SDW: 120.2 mg/ml; Prot: 45.6 mg/ml; A.A: 15.2 mg/ml; Carbohydrates: 2.8 mg/ml) D-amino acid percentage: 35% D-Ala, 13% D-Leu, 57% D-Ser, 44% D-Asx, 40% D-Met, 39% D-Phe, 43% D-Glx.

STPY 8191 Example 2.13

Biomass according to Example 1.5 was diluted to 12.7 g/L. Alkalinization at 0.1 M NaOH was performed. The lysis was incubated for 2 days at 35-40° C. under continuous stirring. (SDW: 12.5 mg/ml; Prot: <0.2 mg/ml; A.A: 0.8 mg/ml; Carbohydrates: 0.1 mg/ml) D-amino acid percentage: 24% D-Ala, 13% D-Leu, 52% D-Ser, 28% D-Asx, 8% D-Met, 8% D-Phe, 23% D-Glx, 6% D-Tyr.

STPY 8191 Example 2.14

Biomass according to Example 1.5 was diluted to 100 g/L. Alkalinization at 0.1 M NaOH was performed. The lysis was incubated for 8 days at 35-40° C. under continuous stirring. (SDW: 41.4 mg/ml; Prot: 3.2 mg/ml; A.A: 4 mg/ml; Carbohydrates: 1.5 mg/ml.)

STPY 8191 Example 2.15

Biomass according to Example 1.5 was diluted to 12.7 g/L. Alkalinization at 0.7 M NaOH was performed. The lysis was incubated for 8 days at 35-40° C. under continuous stirring. (SDW: 52.5 mg/ml; Prot: 0.8 mg/ml; A.A: 3.2 mg/ml; Carbohydrates: 0.6 mg/ml.)

STPY 8191 Example 2.16

Biomass according to Example 1.5 was diluted to 100 g/L. Alkalinization at 0.7 M NaOH was performed. The lysis was incubated for 10 days at 35-40° C. under continuous stirring. (SDW: 147.2 mg/ml; Prot: 53.6 mg/ml; A.A: 24.8 mg/ml; Carbohydrates: 5.4 mg/ml) D-amino acid percentage: 44% D-Ala, 26% D-Leu, 11% D-Ser, 45% D-Asx, 43% D-Met, 42% D-Phe, 46% D-Glx. NOx production in mg of active dry weight/mL: 0.02 mg/mL (C1), 0.2 mg/mL (C2), and 2.0 mg/mL (C3): C1: 9.7 µM, C2: 17.4 µM, C3: 2.5 µM.

STPY 8191 Example 2.17

Biomass according to Example 1.5 was diluted to 12.7 g/L. Alkalinization at 0.1 M NaOH was performed. The lysis was incubated for 10 days at 35-40° C. under continuous stirring. (SDW: 14.7 mg/ml; Prot: 0 mg/ml; A.A: 0.8 mg/ml; Carbohydrates: 0.2 mg/ml.) D-amino acid percentage: 28% D-Ala, 9% D-Ser, 36% D-Asx, 33% D-Met, 32% D-Phe, 31% D-Glx. NOx production in mg of active dry weight/mL, 0.02 mg/mL (C1), 0.2 mg/mL (C2), and 2.0 mg/mL (C3): C1: 5.8 µM, C2: 12.1 µM, C3: 6.8 µM.

STSA 046 Example 2.18

Biomass according to Example 1 was diluted to 68 g/L. Alkalinization at 0.25 M NaOH was performed. The lysis was incubated for 8 days at 35-40° C. under continuous stirring. (SDW: 90.72 mg/ml; Prot: 47.68 mg/ml; A.A: 9.36 mg/ml; Carbohydrates: 2.48 mg/ml.)

STSA 047 Example 2.19

Biomass according to Example 1 is diluted to 68 g/L. Alkalinization at 0.25 M NaOH is performed. The lysis is incubated for 8 days at 35-40° C. under continuous stirring.

STSA 047 Example 2.20

Biomass according to Example 1 is diluted to 60 g/L. Alkalinization at 0.33 M NaOH is performed. The lysis is incubated for 2 days at 35-40° C. under continuous stirring.

STSA 048 Example 2.21

Biomass according to Example 1 is diluted to 62 g/L. Alkalinization at 0.33 M NaOH is performed. The lysis is incubated for 8 days at 35-40° C. under continuous stirring.

STPY 8191 Example 2.22

Biomass according to Example 1.5 is diluted to 55 g/L. Alkalinization at 0.33 M NaOH is performed. The lysis is incubated for 4 days at 35-40° C. under continuous stirring.

STPN 7978 Example 2.23

Biomass according to Example 1.5 was diluted to 38.7 g/L. Alkalinization at 0.25 M NaOH was performed. The lysis was incubated for 8 days at 35-40° C. under continuous stirring. (SDW: 66.4 mg/ml; Prot: 25.4 mg/ml; A.A: 6.0 mg/ml; Carbohydrates: 2.5 mg/ml.) NOx production in mg of active dry weight/mL, 0.02 mg/mL (C1), 0.2 mg/mL (C2), and 2.0 mg/mL (C3): C1: 10.2 µM, C2: 20.7 µM, C3: 20.8 µM.

STPN 7978 Example 2.24

Biomass according to Example 1.5 was diluted to 30 g/L. Alkalinization at 0.022 M NaOH was performed. The lysis was incubated for 8 days at 35-40° C. under continuous stirring. (SDW: 30.4 mg/ml; Prot: 2.20 mg/ml; Carbohydrates: 0.40 mg/ml.)

STPN 7978 Example 2.25

Biomass according to Example 1.5 was diluted to 60 g/L. Alkalinization at 0.7 M NaOH was performed. The lysis was incubated for 2 days at 35-40° C. under continuous stirring. (SDW: 59 mg/ml; Prot: 17 mg/ml; A.A: 7.0 mg/ml; Carbohydrates 1.8 mg/ml.) NOx production in mg of active dry weight/mL, 0.02 mg/mL (C1), 0.2 mg/mL (C2), and 2.0 mg/mL (C3): C1: 9.1 µM, C2: 13.4 µM, C3: 1.4 µM.

STPN 7978 Example 2.26

Biomass according to Example 1.5 was diluted to 12.5 g/L. Alkalinization at 0.1 M NaOH was performed. The lysis was incubated for 2 days at 35-40° C. under continuous stirring. (SDW: 17.8 mg/ml; Prot: <0.2 mg/ml; A.A: 2.0 mg/ml; Carbohydrates: 0.7 mg/ml.)

STPN 7978 Example 2.27

Biomass according to Example 1.5 was diluted to 60 g/L. Alkalinization at 0.1 M NaOH was performed. The lysis was incubated for 8 days at 35-40° C. under continuous stirring. (SDW: 43.6 mg/ml; Prot: 6 mg/ml; A.A: 10 mg/ml; Carbohydrates: 1.5 mg/ml.)

STPN 7978 Example 2.28

Biomass according to Example 1.5 was diluted to 12.5 g/L. Alkalinization at 0.7 M NaOH was performed. The lysis was incubated for 8 days at 35-40° C. under continuous stirring. (SDW: 55.4 mg/ml; Prot: 2 mg/ml; A.A: 4 mg/ml; Carbohydrates 0.7 mg/ml.)

STPN 7978 Example 2.29

Biomass according to Example 1.5 was diluted to 60 g/L. Alkalinization at 0.7 M NaOH was performed. The lysis was incubated for 10 days at 35-40° C. under continuous stirring. (SDW: 118.4 mg/ml; Prot: 31 mg/ml; A.A: 19 mg/ml; Carbohydrates: 4.1 mg/ml.) NOx production in mg of active dry weight/mL, 0.02 mg/mL (C1), 0.2 mg/mL (C2), and 2.0 mg/mL (C3): C1: 5.8 µM, C2: 12.1 µM, C3: 2.8 µM.

STPN 7978 Example 2.30

Biomass according to Example 1.5 was diluted to 12.5 g/L. Alkalinization at 0.1 M NaOH was performed. The lysis was incubated for 10 days at 35-40° C. under continuous stirring. (SDW: 18.4 mg/ml; Prot: <0.2 mg/ml; A.A: 2 mg/ml; Carbohydrates: 0.5 mg/ml.)

STPN 7465 Example 2.31

Biomass according to Example 1.5 was diluted to 52.5 g/L. Alkalinization at 0.25 M NaOH was performed. The lysis was incubated for 8 days at 35-40° C. under continuous stirring. (SDW: 69.4 mg/ml; Prot: 32.3 mg/ml; A.A: 6.0 mg/ml; Carbohydrates: 1.7 mg/ml.)

STPN 7466 Example 2.32

Biomass according to Example 1.5 was diluted to 40.0 g/L. Alkalinization at 0.25 M NaOH was performed. The lysis was incubated for 8 days at 35-40° C. under continuous stirring. (SDW: 60.6 mg/ml; Prot: 29.0 mg/ml; A.A: 6.0 mg/ml; Carbohydrates: 1.50 mg/ml.)

STPN 10319 Example 2.33

Biomass according to Example 1.5 was diluted to 41.2 g/L. Alkalinization at 0.25 M NaOH was performed. The lysis was incubated for 8 days at 35-40° C. under continuous stirring. (SDW: 60.4 mg/ml; Prot: 28.4 mg/ml; A.A: 6.0 mg/ml; Carbohydrates 1.1 mg/ml.)

STSA 046 Example 2.34

Biomass according to Example 1.5 was diluted to 58.9 g/L. Alkalinization at 0.25 M NaOH was performed. The lysis was incubated for 8 days at 35-40° C. under continuous stirring. (SDW: 83.2 mg/ml; Prot: 7.2 mg/ml; A.A: 8.39 mg/ml; Carbohydrates: 2.16 mg/ml.)

STSA 047 Example 2.35

Biomass according to Example 1.5 was diluted to 50.4 g/L. Alkalinization at 0.25 M NaOH was performed. The lysis was incubated for 8 days at 35-40° C. under continuous stirring. (SDW: 60.64 mg/ml; Prot: 27.92 mg/ml; A.A: 7.2 mg/ml; Carbohydrates: 3.52 mg/ml.)

STSA 048 Example 2.36

Biomass according to Example 1.5 was diluted to 66.2 g/L. Alkalinization at 0.25 M NaOH was performed. The lysis was incubated for 8 days at 35-40° C. under continuous stirring. (SDW: 72.96 mg/ml; Prot: 36.16 mg/ml; A.A: 7.2 mg/ml; Carbohydrates: 3.28 mg/ml.)

NECA I045 Example 2.37

One aliquot of NeCa 1045 from Example 1.4 containing 223 g of bacterial material was thawed at room temperature and diluted with a saline solution (8 g/L NaCl) to reach 22.8 g/L. Alkalinization at 0.2 M NaOH was performed. The lysis was incubated for 192 hours at 35-40° C. under continuous stirring. During the lysis, the pH was monitored so as not to decrease by more than 0.5 pH units. (SDW: 41.29 mg/mL; Prot: 17.45 mg/mL; A.A.: 3.41 mg/mL; Carbohydrates: 3.4 mg/mL.) NOx production in mg of active dry weight/mL, 0.02 mg/mL (C1), 0.2 mg/mL (C2), and 2.0 mg/mL (C3): C1: 4.2 µM, C2: 14.8 µM, C3: 13.4 µM.

NECA I045 Example 2.38

Biomass according to Example 1.4 was diluted to 20.5 g/L. Alkalinization at 0.2 M NaOH was performed. The lysis was incubated for 3 days at 35-40° C. under continuous stirring. (SDW: 36.6 mg/ml; Prot: 16.4 mg/ml; A.A: 3.63 mg/ml; Carbohydrates: 0.77 mg/ml.)

NECA I045 Example 2.39

Biomass according to Example 1.4 was diluted to 51.0 g/L. Alkalinization at 0.7 M NaOH was performed. The lysis was incubated for 2 days at 35-40° C. under continuous stirring. (SDW: 75.69 mg/ml; Prot: 30.8 mg/ml; A.A: 10.8 mg/ml; Carbohydrates: 1.14 mg/ml.) D-amino acid percentage: 40% D-Ala, 45% D-Asx, 42% D-Met, 40% D-Phe, 46% D-Glx, 48% D-Lys. NOx production in mg of active dry weight/mL, 0.02 mg/mL (C1), 0.2 mg/mL (C2), and 2.0 mg/mL (C3): C1: 4.9 µM, C2: 14.3 µM, C3: 3.6 µM.

NECA I045 Example 2.40

Biomass according to Example 1.4 was diluted to 13 g/L. Alkalinization at 0.1 M NaOH was performed. The lysis was incubated for 2 days at 35-40° C. under continuous stirring. (SDW: 15.08 mg/ml; Prot: 7.7 mg/ml; A.A: 1.5 mg/ml; Carbohydrates: 0.28 mg/ml.) D-amino acid percentage: 21% D-Ala, 67% D-Ser, 31% D-Asx, 25% D-Met, 12% D-Lys.

NECA I045 Example 2.41

Biomass according to Example 1.4 was diluted to 51.0 g/L. Alkalinization at 0.1 M NaOH was performed. The lysis was incubated for 8 days at 35-40° C. under continuous stirring. (SDW: 41.23 mg/ml; Prot: 26.2 mg/ml; A.A: 4.6 mg/ml; Carbohydrates: 0.98 mg/ml.)

NECA I045 Example 2.42

Biomass according to Example 1.4 was diluted to 13 g/L. Alkalinization at 0.7 M NaOH was performed. The lysis was incubated for 8 days at 35-40° C. under continuous stirring. (SDW: 48.43 mg/ml; Prot: 7.7 mg/ml; A.A: 4.3 mg/ml; Carbohydrates: 0.22 mg/ml.)

NECA I045 Example 2.43

Biomass according to Example 1.4 was diluted to 51.0 g/L. Alkalinization at 0.7 M NaOH was performed. The lysis was incubated for 10 days at 35-40° C. under continuous stirring. (SDW: 83.02 mg/ml; Prot: 28.9 mg/ml; A.A: 15 mg/ml; Carbohydrates: 1.11 mg/ml.) D-amino acid percentage: 44% D-Ala, 48% D-Ser, 47% D-Asx, 45% D-Met, 43% D-Phe, 50% D-Glx. NOx production in mg of active dry weight/mL, 0.02 mg/mL (C1), 0.2 mg/mL (C2), and 2.0 mg/mL (C3): C1: 5.1 µM, C2: 12.0 µM, C3: 7.5 µM.

NECA I045 Example 2.44

Biomass according to Example 1.4 was diluted to 13 g/L. Alkalinization at 0.1 M NaOH was performed. The lysis was incubated for 10 days at 35-40° C. under continuous stirring. (SDW: 15.26 mg/ml; Prot: 8.6 mg/ml; A.A: 1.8 mg/ml; Carbohydrates 0.22 mg/ml.) D-amino acid percentage: 31% D-Ala, 42% D-Ser, 38% D-Asx, 36% D-Met, 35% D-Phe, 37% D-Glx. NOx production in mg of active dry weight/mL, 0.02 mg/mL (C1), 0.2 mg/mL (C2), and 2.0 mg/mL (C3): C1: 4.1 µM, C2: 13.9 µM, C3: 6.0 µM.

NECA I045 Example 2.45

Biomass according to Example 1.4 was diluted to 9 g/L. Alkalinization at 0.066 M NaOH was performed. The lysis was incubated for 8 days at 35-40° C. under continuous stirring. (SDW: 20.62 mg/ml; Prot: 5.57 mg/ml; Carbohydrates: 0.06 mg/ml.)

NECA NCTC3622 Example 2.46

Biomass according to Example 1.4 was diluted to 20.1 g/L. Alkalinization at 0.2 M NaOH was performed. The lysis was incubated for 8 days at 35-40° C. under continuous stirring. (SDW: 35.69 mg/ml; Prot: 14.25 mg/ml; A.A: 3.4 mg/ml; Carbohydrates: 0.71 mg/ml.)

NECA NCTC3625 Example 2.47

Biomass according to Example 1.4 was diluted to 9.7 g/L. Alkalinization at 0.2 M NaOH was performed. The lysis was incubated for 8 days at 35-40° C. under continuous stirring. (SDW: 38.83 mg/ml; Prot: 15.54 mg/ml; A.A: 3.4 mg/ml; Carbohydrates: 0.95 mg/ml.)

KLPN 204 Example 2.48

One aliquot of KlPn 204 Example 1.3 containing 440 g of bacterial material was thawed at room temperature and diluted with a saline solution (8 g/L NaCl) to reach 37.7 g/L. Alkalinization at 0.2 M NaOH was performed. The lysis was incubated for 192 hours at 35-40° C. under continuous stirring. During the lysis, the pH was monitored so as not to decrease by more than 0.5 pH units. (SDW: 51.77 mg/mL; Prot: 27.66 mg/mL; A.A.: 4.2 mg/mL; Carbohydrates: 1.03 mg/mL). NOx production in mg of active dry weight/mL, 0.02 mg/mL (C1), 0.2 mg/mL (C2), and 2.0 mg/mL (C3): C1: 0.6 µM, C2: 2.8 µM, C3: 1.8 µM.

KLPN 204 Example 2.49

Biomass according to Example 1.3 was diluted to 9 g/L. Alkalinization at 0.013 N NaOH was performed. The lysis was incubated for 8 days at 35-40° C. under continuous stirring. (SDW: 25.71 mg/ml; Prot: 4.91 mg/ml; Carbohydrates 0.51 mg/ml.)

KLPN 204 Example 2.50

Biomass according to Example 1.3 was diluted to 99 g/L. Alkalinization at 0.1 M NaOH was performed. The lysis was incubated for 2 days at 35-40° C. under continuous stirring. (SDW: 50.63 mg/ml; Prot: 15.4 mg/ml; A.A: 2.9 mg/ml; Carbohydrates: 2.1 mg/ml.) D-amino acid percentage: 5% D-Ala, 6% D-Asx.

KLPN 204 Example 2.51

Biomass according to Example 1.3 was diluted to 13 g/L. Alkalinization at 0.7 M NaOH was performed. The lysis was incubated for 2 days at 35-40° C. under continuous stirring. (SDW: 52.69 mg/ml; Prot: 5.7 mg/ml; A.A: 2.3 mg/ml; Carbohydrates: 0.3 mg/ml.) D-amino acid percentage: 36% D-Ala, 8% D-Ser, 45% D-Asx, 7% D-Met, 27% D-Phe, 40% D-Glx, 29% D-Lys. NOx production in mg of active dry weight/mL, 0.02 mg/mL (C1), 0.2 mg/mL (C2), and 2.0 mg/mL (C3): C1: 0.5 µM, C2: 0.8 µM, C3: 6.0 µM.

KLPN 204 Example 2.52

Biomass according to Example 1.3 was diluted to 99 g/L. Alkalinization at 0.7 M NaOH was performed. The lysis was incubated for 8 days at 35-40° C. under continuous stirring. (SDW: 136.34 mg/ml; Prot: 58.9 mg/ml; A.A: 20.6 mg/ml; Carbohydrates: 3.4 mg/ml.)

KLPN 204 Example 2.53

Biomass according to Example 1.3 was diluted to 13 g/L. Alkalinization at 0.1 M NaOH was performed. The lysis was incubated for 8 days at 35-40° C. under continuous stirring. (SDW: 18.06 mg/ml; Prot: 6.3 mg/ml; A.A: 1.1 mg/ml; Carbohydrates: 0.3 mg/ml.) NOx production in mg of active dry weight/mL, 0.02 mg/mL (C1), 0.2 mg/mL (C2), and 2.0 mg/mL (C3): C1: 0.5 µM, C2: 1.6 µM, C3: 1.9 µM.

KLPN 204 Example 2.54

Biomass according to Example 1.3 was diluted to 99 g/L. Alkalinization at 0.1 M NaOH was performed. The lysis was incubated for 10 days at 35-40° C. under continuous stirring. (SDW: 58.06 mg/ml; Prot: 20 mg/ml; A.A: 4.6 mg/ml; Carbohydrates 2.7 mg/ml.)

KLPN 204 Example 2.55

Biomass according to Example 1.3 was diluted to 13 g/L. Alkalinization at 0.7 M NaOH was performed. The lysis was incubated for 10 days at 35-40° C. under continuous stirring. (SDW: 52.57 mg/ml; Prot: 5.7 mg/ml; A.A: 4.0 mg/ml; Carbohydrates: 0.3 mg/ml.) D-amino acid percentage: 43% D-Ala, 25% Val, 5% D-Ser, 46% D-Asx, 46% D-Met, 45% D-Phe, 44% D-Glx, 38% D-Lys. NOx production in mg of active dry weight/mL, 0.02 mg/mL (C1), 0.2 mg/mL (C2), and 2.0 mg/mL (C3): C1: 0.5 µM, C2: 0.6 µM, C3: 2.6 µM.

KLPN 5056 Example 2.56

Biomass according to Example 1.3 was diluted to 39.4 g/L. Alkalinization at 0.2 M NaOH was performed. The lysis was incubated for 8 days at 35-40° C. under continuous stirring. (SDW: 52.69 mg/ml; Prot: 27.83 mg/ml; A.A: 4.0 mg/ml; Carbohydrates: 1.09 mg/ml.)

KLPN 5050 Example 2.57

Biomass according to Example 1.3 was diluted to 34.2 g/L. Alkalinization at 0.2 M NaOH was performed. The lysis was incubated for 8 days at 35-40° C. under continuous stirring. (SDW: 48.23 mg/ml; Prot: 26.57 mg/ml; A.A: 4.0 mg/ml; Carbohydrates: 1.03 mg/ml.)

STAU I051 Example 2.58

One aliquot of StAu I051 from Example 1.2 containing 375 g of bacterial material was thawed at room temperature and diluted with a saline solution (8 g/L NaCl) to reach 55.2 g/L. Alkalinization at 0.2 M NaOH was performed. The lysis was incubated for 192 hours at 35-40° C. under continuous stirring. During the lysis, the pH should was monitored so as not to decrease by more than 0.5 pH units. (SDW: 66.4 mg/mL; Prot: 34.08 mg/mL; A.A.: 6.4 mg/mL; Carbohydrates: 0.64 mg/mL.) NOx production in mg of active dry weight/mL, 0.02 mg/mL (C1), 0.2 mg/mL (C2), and 2.0 mg/mL (C3): C1: 0.6 µM, C2: 0.8 µM, C3: 1.4 µM.

STAU I051 Example 2.59

Biomass according to Example 1.2 was diluted to 51 g/L. Alkalinization at 0.2 M NaOH was performed. The lysis was incubated for 9 days at 35-40° C. under continuous stirring. (SDW: 65.31 mg/ml; Prot: 25.56 mg/ml; A.A: 6.57 mg/ml; Carbohydrates: 0.98 mg/ml.)

STAU I051 Example 2.60

Biomass according to Example 1.2 was diluted to 81 g/L. Alkalinization at 0.7 M NaOH was performed. The lysis was incubated for 2 days at 35-40° C. under continuous stirring.

(SDW: 137.2 mg/ml; Prot: 51.2 mg/ml; A.A: 20.8 mg/ml; Carbohydrates: 1.6 mg/ml.) D-amino acid percentage: 51% D-Ala, 11% D-Ser, 43% D-Asx, 37% D-Met, 35% D-Phe, 43% D-Glx. NOx production in mg of active dry weight/mL, 0.02 mg/mL (C1), 0.2 mg/mL (C2), and 2.0 mg/mL (C3): C1: 0.6 µM, C2: 0.8 µM, C3: 1.3 µM.

STAU I051 Example 2.61

Biomass according to Example 1.2 was diluted to 13 g/L. Alkalinization at 0.7 M NaOH was performed. The lysis was incubated for 8 days at 35-40° C. under continuous stirring. (SDW: 55.7 mg/ml; Prot: 4.8 mg/ml; A.A: 4.8 mg/ml; Carbohydrates: 0.2 mg/ml.)

STAU I051 Example 2.62

Biomass according to Example 1.2 was diluted to 81 g/L. Alkalinization at 0.7 M NaOH was performed. The lysis was incubated for 8 days at 35-40° C. under continuous stirring. (SDW: 130.1 mg/ml; Prot: 47.2 mg/ml; A.A: 24.8 mg/ml; Carbohydrates: 1.4 mg/ml.)

STAU I051 Example 2.63

Biomass according to Example 1.2 was diluted to 13 g/L. Alkalinization at 0.1 M NaOH was performed. The lysis was incubated for 8 days at 35-40° C. under continuous stirring. (SDW: 18.4 mg/ml; Prot: 4.8 mg/ml; A.A: 2.4 mg/ml; Carbohydrates: 0.2 mg/ml.) NOx production in mg of active dry weight/mL, 0.02 mg/mL (C1), 0.2 mg/mL (C2), and 2.0 mg/mL (C3): C1: 0.5 µM, C2: 0.6 µM, C3: 1.3 µM.

STAU I051 Example 2.64

Biomass according to Example 1.2 was diluted to 81 g/L. Alkalinization at 0.7 M NaOH was performed. The lysis was incubated for 10 days at 35-40° C. under continuous stirring. (SDW: 134.6 mg/ml; Prot: 48 mg/ml; A.A: 25.6 mg/ml; Carbohydrates: 1.5 mg/ml.) D-amino acid percentage: 56% D-Ala, 10% D-Ser, 45% D-Asx, 42% D-Met, 39% D-Phe, 73% D-Tyr, 49% D-Glx. NOx production in mg of active dry weight/mL, 0.02 mg/mL (C1), 0.2 mg/mL (C2), and 2.0 mg/mL (C3): C1: 0.6 µM, C2: 0.7 µM, C3: 1.1 µM.

STAU I051 Example 2.65

Biomass according to Example 1.2 was diluted to 13 g/L. Alkalinization at 0.1 M NaOH was performed. The lysis was incubated for 10 days at 35-40° C. under continuous stirring. (SDW: 17.9 mg/ml; Prot: 5.6 mg/ml; A.A: 2.4 mg/ml; Carbohydrates: 0.2 mg/ml.) NOx production in mg of active dry weight/mL, 0.02 mg/mL (C1), 0.2 mg/mL (C2), and 2.0 mg/mL (C3): C1: 0.5 µM, C2: 0.6 µM, C3: 3.7 µM.

STAU I049 Example 2.66

Biomass according to Example 1.2 was diluted to 52.8 g/L. Alkalinization at 0.2 M NaOH was performed. The lysis was incubated for 8 days at 35-40° C. under continuous stirring. (SDW: 70.08 mg/ml; Prot: 34.4 mg/ml; A.A: 6.4 mg/ml; Carbohydrates: 0.64 mg/ml.)

STAU I050 Example 2.67

Biomass according to Example 1.2 was diluted to 47.5 g/L. Alkalinization at 0.2 M NaOH was performed. The lysis was incubated for 8 days at 35-40° C. under continuous stirring. (SDW: 64.32 mg/ml; Prot: 32.24 mg/ml; A.A: 6.4 mg/ml; Carbohydrates: 0.64 mg/ml.)

STAU I050 Example 2.68

Biomass according to Example 1.2 was diluted to 48.5 g/L. Alkalinization at 0.033 M NaOH was performed. The lysis was incubated for 8 days at 35-40° C. under continuous stirring.

STAU I052 Example 2.69

Biomass according to Example 1.2 was diluted to 56.9 g/L. Alkalinization at 0.2 M NaOH was performed. The lysis was incubated for 8 days at 35-40° C. under continuous stirring. (SDW: 62.72 mg/ml; Prot: 30.8 mg/ml; A.A: 6.4 mg/ml; Carbohydrates: 0.72 mg/ml.)

STAU I053 Example 2.70

Biomass according to Example 1.2 was diluted to 67.3 g/L. Alkalinization at 0.2 M NaOH was performed. The lysis was incubated for 8 days at 35-40° C. under continuous stirring. (SDW: 68.8 mg/ml; Prot: 32.24 mg/ml; A.A: 6.4 mg/ml; Carbohydrates: 1.2 mg/ml.)

STAU I050 Example 2.71

Biomass according to Example 1.2 was diluted to 63.6 g/L. Alkalinization at 0.2 M NaOH was performed. The lysis was incubated for 8 days at 35-40° C. under continuous stirring. (SDW: 68.96 mg/ml; Prot: 24.56 mg/ml; A.A: 6.4 mg/ml; Carbohydrates: 2.56 mg/ml.)

Example 3

Purification of Lysates

Example 3.1

Clarified Extract of a Gram Negative and a Gram Positive Strain

2 L of Example 2.57 and 2 L of Example 2.66 were mixed together, pH was adjusted to 12.0 with addition of concentrated HCl, and the mixture was diluted with 2 L of 8 g/L NaCl solution. The diluted mixture was transferred to a microfiltration (MF) tank. The microfiltration unit used a 0.45 micron tangential flow filtration filter (PALL Procette PES 0.45 micron) in a serpentine mode (See FIG. 1). The cross flow was adjusted at 2000 L/h m$^2$ (LHM) and the trans-membrane pressure (TMP) at 1.3 bar. The microfiltration permeate was transferred to an ultrafiltration (UF) tank.

Once the volume of the mixture in the microfiltration tank reached the half of the initial volume, the UF unit was started. The ultrafiltration unit used a 30 kDa tangential flow filtration filter (PALL Centrasette PES 30 kD). The crossflow was adjusted at 1000 LHM and the TMP at 0.5 bar.

The volumes in the MF and UF tanks were maintained at the same level. At each diafiltration volume, the protein concentration was measured by the Bradford method. [The Bradford method is standard in the art. There is no need to cite a reference unless different ways of doing the method give significantly different results.] In the UF Tank the Bradford protein content was 26.8 mg/mL after 1 diafiltration volume (DFV), 34.8 mg/mL after 4 DFV, and 37.2 mg/mL after 9 DFV. The permeate flux of microfiltration during the diafiltration was 15 LHM. After 14 diafiltration volumes, the UF was stopped, and the product was concentrated in the MF tank. The product contained 15.9 mg/mL protein. The product was then diluted to 7.4 mg/mL and filtered through a 0.2 micron sterile filter. (Solubilized dry residue (SDR): 21.0 mg/mL, Prot: 7.4 mg/mL, A.A.: 1.2 mg/mL, glucides (Carbohydrates): 0.3 mg/mL, Chloride: 4.6 mg/ml.) NOx production in mg of Lowry protein mg/mL, 0.03 mg/mL (C1), 0.3 mg/mL (C2), and 3.0 mg/mL (C3): C1: 5.8 µM, C2: 11.4 µM, C3: 1.2 µM.

Example 3.2

Klba Mono Strain 4 kg of Example 2.57 was adjusted to pH 12.0 and diluted with 4 L of 8 g/L NaCl solution. The diluted lysate was transferred to a microfiltration tank.

Microfiltration parameters were: Cross Flow 2000 LHM, TMP 1.3 bar, cut off: 0.45 µm. Ultrafiltration parameters were: Cross Flow 1000 LHM, TMP 0.5 bar, cut off: 30 kDa, number of diafiltration volumes: 8.

The product was diluted to 7.0 mg/mL and filtered through a 0.2 micron sterile filter. (SDR: 18.0 mg/mL, Prot: 7.0 mg/mL, A.A.: 0.8 mg/mL, Carbohydrates: 0.3 mg/mL.) NOx production in mg of Lowry protein/mL, 0.03 mg/mL (C1), 0.3 mg/mL (C2), and 3.0 mg/mL (C3): C1: 5.2 µM, C2: 9.8 µM, C3: 1.1 µM.

Example 3.3

*Moraxella* Mono Strain 2 kg of Example 2.37 was adjusted to pH 10.7 and diluted with 3 L of 8 g/L NaCl solution. The diluted lysate was transferred to the microfiltration tank.

Microfiltration parameters were: Cross Flow 2000 LHM, TMP 1.3 bar, cut off: 0.45 µm. Ultrafiltration parameters were: Cross Flow 1000 LHM, TMP 0.5 bar, cut off: 30 kDa, number of diafiltration volumes: 8.

The product was diluted to 7.0 mg/mL and filtered through a 0.2 micron sterile filter. (SDR: 19.4 mg/mL, Prot: 6.8 mg/mL.)

Example 3.4

Pneumoniae Mono Strain 5.0 kg of Example 2.32 was adjusted to pH 12.27 and diluted with 5.0 Liters of 8 g/L NaCl solution. The diluted lysate was transferred to a microfiltration tank.

Microfiltration parameters were: Cross Flow 2000 LHM, TMP 1.3 bar, cut off: 0.45 µm. Ultrafiltration parameters were: Cross Flow 1000 LHM, TMP 0.5 bar, cut off: 30 kDa, number of diafiltration volumes: 8.

The product was diluted to 7.0 mg/mL and filtered through a 0.2 micron sterile filter. (SDR: 23.3 mg/mL, Prot: 4.3 mg/ml.)

Example 3.5

500 ml of Example 2.45, 500 ml of Example 2.47, and 500 ml of Example 2.37 are mixed and centrifuged at 9000×g. The supernatant is filtered through successive filters with porosities of 0.8 µm, 0.45 µm and 0.2 µm. The pH is adjusted to 10.5 with HCl.

Example 3.6

300 ml of the lysate of Example 2.23, 300 ml of Example 2.31, 300 ml of Example 2.32, and 300 ml of Example 2.33 were mixed and centrifuged for 30 minutes at 9000×g. The supernatant was filtered through successive filters with porosities of 0.8 µm, 0.45 µm and 0.2 µm. The pH was adjusted to 10.5 with HCl. Analytical results: (SDR: 63.60 mg/mL, Prot: 23.00 mg/mL, A.A.: 6.00 mg/mL, Carbohydrates: 1.60 mg/ml.)

Example 3.7

300 ml of Example 2.48, 300 ml of Example 2.56, and 300 ml of Example 2.57 were mixed and centrifuged at 9000×g. The supernatant was filtered through successive filters with porosities of 0.8 µm, 0.45 µm and 0.2 µm. The pH was adjusted to 10.5 with HCl. (SDR: 50.40 mg/mL, Prot: 22.30 mg/mL, A.A.: 4.0 mg/mL, Carbohydrates: 0.97 mg/ml.) NOx production in mg of solubilized dry weight/mL, 0.01 mg/mL (C1), 0.1 mg/mL (C2), and 1.0 mg/mL (C3): C1: 1.06 µM, C2: 3.19 µM, C3: 7.62 µM.

Example 3.8

200 ml of Example 2.58, 200 ml of Example 2.66, 200 ml of Example 2.67, 200 ml of Example 2.69, 200 ml of Example 2.70 and 200 ml of Example 2.71 were mixed and centrifuged for at 9000×g. The supernatant was filtered through successive filters with porosities of 0.8 µm, 0.45 µm and 0.2 µm. The pH was adjusted to 10.5 with HCl. (SDR: 65.12 mg/mL, Prot: 24.80 mg/mL, A.A.: 7.2 mg/mL, Carbohydrates: 1.12 mg/ml.) NOx production in mg of solubilized dry weight/mL, 0.01 mg/mL (C1), 0.1 mg/mL (C2), and 1.0 mg/mL (C3): C1: 0.76 µM, C2: 1.16 µM, C3: 3.79 µM.

Example 3.9

500 ml of Example 2.46, 500 ml of Example 2.47 and 500 ml of Example 2.37 were mixed and centrifuged for at 9000×g. The supernatant was filtered through successive filters with porosities of 0.8 µm, 0.45 µm and 0.2 µm. The pH was adjusted to 10.5 with HCl. (SDR: 38.15 mg/mL, Prot: 13.5 mg/mL, A.A.: 3.4 mg/mL, Carbohydrates: 0.80 mg/ml.) NOx production in mg of solubilized dry weight/mL, 0.01 mg/mL (C1), 0.1 mg/mL (C2), and 1.0 mg/mL (C3): C1: 2.25 µM, C2: 5.25 µM, C3: 14.21 µM.

Example 3.10

500 ml of Example 2.34, 500 ml of Example 2.35, 500 ml of Example 2.36, and 500 ml of Example 2.10 were mixed and centrifuged at 9000×g. The supernatant was filtered through successive filters with porosities of 0.8 µm, 0.45 µm and 0.2 µm. The pH was adjusted to 10.5 with HCl. (SDR: 69.6 mg/mL, Prot: 28.00 mg/mL, A.A.: 7.2 mg/mL, Carbohydrates: 2.48 mg/ml.) NOx production in mg of solubilized dry weight/mL, 0.01 mg/mL (C1), 0.1 mg/mL (C2), and 1.0 mg/mL (C3): C1: 0.95 µM, C2: 1.21 µM, C3: 4.44 µM.

Example 3.11

10 ml of the lysate of Example 2.61 and 10 ml of Example 2.27 were centrifuged at 9000×g, separately. The supernatants were filtered through successive filters with porosities of 0.8 µm, 0.45 µm and 0.2 µm. 3 mL of each supernatant were mixed. The pH was adjusted to 7.2 with HCl. NOx production in mg of solubilized dry weight/mL, 0.01 mg/mL (C1), 0.1 mg/mL (C2), and 1.0 mg/mL (C3): C1: 0.34 µM, C2: 0.66 µM, C3: 1.33 µM.

Example 3.12

10 ml of Example 2.58 and 10 ml of Example 2.61 were centrifuged at 9000×g, separately. The supernatants were filtered through successive filters with porosities of 0.8 µm, 0.45 µm and 0.2 µm. 3 mL of each supernatant were mixed together. The pH was adjusted to 7.6 with HCl. NOx production in mg of solubilized dry weight/mL, 0.01 mg/mL (C1), 0.1 mg/mL (C2), and 1.0 mg/mL (C3): C1: 0.40 µM, C2: 0.44 µM, C3: 0.71 µM.

Example 3.13

10 ml of Example 2.9 and 10 ml of Example 2.8 were centrifuged at 9000×g, separately. The supernatants were filtered through successive filters with porosities of 0.8 µm, 0.45 µm and 0.2 µm. 1.5 mL of the first lysate (Example 2.9) was mixed with 4.5 mL of the second (Example 2.8). The pH was adjusted to 7.2 with HCl. NOx production in mg of solubilized dry weight/mL, 0.01 mg/mL (C1), 0.1 mg/mL (C2), and 1.0 mg/mL (C3): C1: 8.7 µM, C2: 16.90 µM, C3: 21.1 µM.

Example 3.14

10 ml of Example 2.2 and 10 ml of Example 2.8 were centrifuged at 9000×g, separately. The supernatant was filtered through successive filters with porosities of 0.8 µm, 0.45 µm and 0.2 µm. 3 mL of each supernatant were mixed together. The pH was adjusted to 7.5 with HCl. NOx production in mg of solubilized dry weight/mL, 0.01 mg/mL (C1), 0.1 mg/mL (C2), and 1.0 mg/mL (C3): C1: 9.2 µM, C2: 11.3 µM, C3: 17.2 µM.

Example 3.15

13.2 L of lysis from Example 2.2, 48.6 L of mixture lysis from Example 3.9, 36.6 L of mixture lysis from Example 3.7, 36 L of mixture lysis from Example 3.8, 14.4 L of Example 3.6, and 18.4 L of Example 3.10 were mixed together and diluted to 334.4 L with a 8 g/L NaCl solution. The solution was purified by tangential flow filtration in a double microfiltration and ultrafiltration loops system, as described in Example 3.1. (SDW: 21.0 mg/ml; Prot: 6.4 mg/ml; A.A: 1.9 mg/ml; Carbohydrates 0.45 mg/ml.) D-amino acid percentage: 42% D-Ala, 12% Leu, 53% D-Ser, 37% D-Asx, 35% D-Met, 32% D-Phe, 28% D-Glx, 8% D-Tyr, 16% Lys. NOx production in mg of Lowry protein mg/mL, 0.03 mg/mL (C1), 0.3 mg/mL (C2), and 3.0 mg/mL (C3): C1: 9.3 µM, C2: 14.3 µM, C3: 11.5 µM.

Example 4

Comparative Example of Bacterial Lysis in Lower pH Conditions

Example 4 represents a process which was performed in alkaline conditions outside the scope of the invention. NaOH concentrations used to perform the lysis of bacteria were lower than 0.1%, leading to lower pH values.

The following lysates were mixed: 1.18 kg of Example 2.24, 3.0 kg of Example 2.49, 2.95 kg of Example 2.69, 1.08 Kg of Example 2.4, 1.51 kg of Example 2.11, and 3.98 kg of Example 2.45. Six kilograms of the mixture was diluted to 12 kg with NaCl Solution 8 g/L and the pH was adjusted to pH 12.0. Microfiltration parameters were: Cross Flow 2000 LHM, TMP 1.3 bar, cut off: 0.45 µm. Ultrafiltration parameters were: Cross Flow 1000 LHM, TMP 0.5 bar, cut off: 30 kDa, number of diafiltration volumes: 12. (SDR: 19.4 mg/ml, Prot: 3.1 mg/ml, A.A.: 2.0 mg/ml, Carbohydrates: 0.1 mg/ml, LAL: 20140 EU/ml.) NOx production in mg of active dry weight/mL, 0.03 mg/mL (C1), 0.3 mg/mL (C2), and 3.0 mg/mL (C3): C1: 9.3 µM C2: 14.3 µM C3: 11.5 µM.

Example 5

Lysis of *Lactobaccilus helveticus*

Aliquots of bacterial biomass of *Lactobacillus helveticus* obtained by fermentation on a vegetal medium are thawed at room temperature and diluted with purified water to reach 80 g/L of dry weight concentration. Alkalinization at 0.2 M NaOH is performed. The lysis is incubated for 2 days at 35-40° C. under continuous stirring. During the lysis, the pH is monitored so as not to decrease by more than 0.5 pH units.

Example 6

Immunoprotection Against Aerosol Influenza Virus Infection in Mice

This experiment was aimed at investigating the non-specific immunological activity of certain embodiments of the invention by evaluating their efficacy against a virus, namely H1N1. Six-week-old female BALB/c mice were purchased from Bundesinstitut für Risikobewertung, Berlin, and were used for all experiments. The animals were maintained under normal conditions at ambient temperature of 22° C. and a relative humidity of 60±5%. The light program was set on a light-dark cycle of 12:12 hours. Animals were fed with a standard diet of pellets (Altromin 1314, Altromin, Lage, Germany) and tap water was provided ad libitum.

Pre-Treatment

A total of 60 mice were divided into 3 groups of 20 mice each, with 2 treatment groups and 1 control group. Animals (2 groups) were pre-treated with either 1 mg or 10 mg per mouse once daily for 10 consecutive days, or PBS control (1 group). At the end of the pre-treatment, all mice were given an aerosol of a mouse-adapted A/PR/8/34 (H1N1) influenza virus. The $LD_{50}$ for mice using this strain is usually $10^{-4.5}$ by the intranasal and $10^{-1.7}$ by the aerosol route. The dosage used for challenge infection in these experiments was selected to provide a dilution capable of causing clear symptomatic influenza virus infection, but not 100% lethality.

Figure 3:
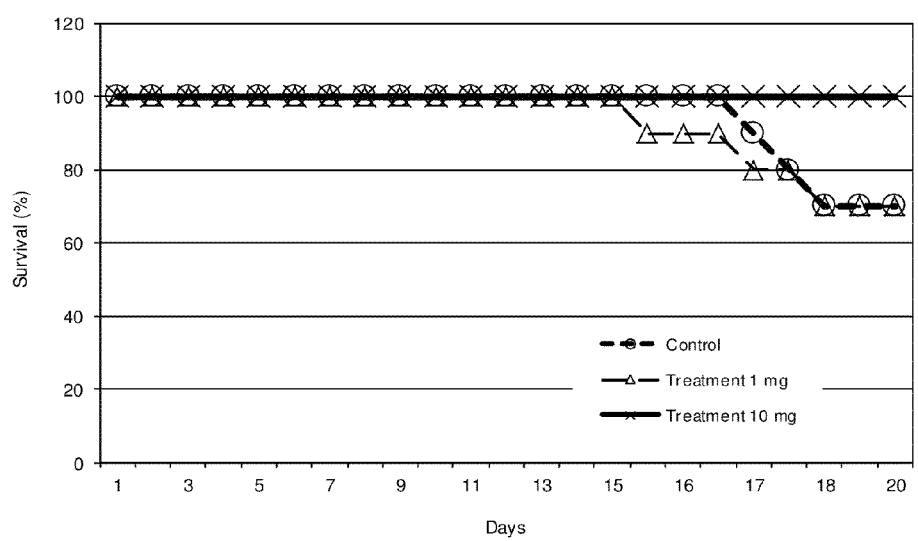
FIG. 3: Survival of mice challenged with virus H1N1 during 3 weeks after the infection. Mc Nemar: test *p=0.023 for 10 mg treatment vs control.
Figure 4:
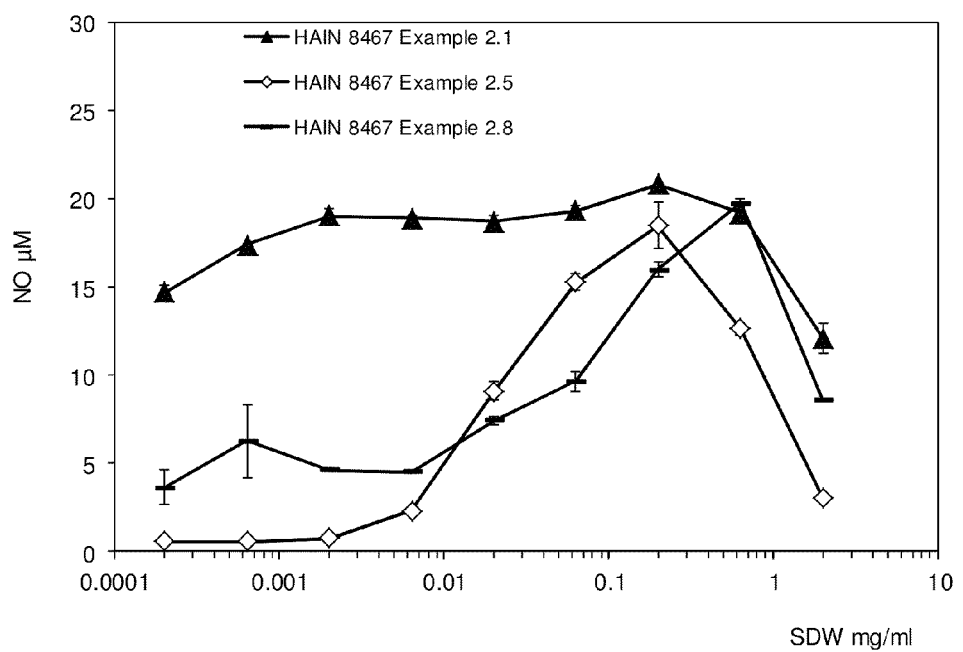
FIG. 4: Effects of NaOH concentration, amount of biomass (expressed in grams dry weight per milliliter), and duration of lysis (in hours) on the biological activities of purified HAIN 8467 extracts (Examples 2.1, 2.5, 2.8) in a nitric oxide bioassay in murine macrophages.
Figure 5:
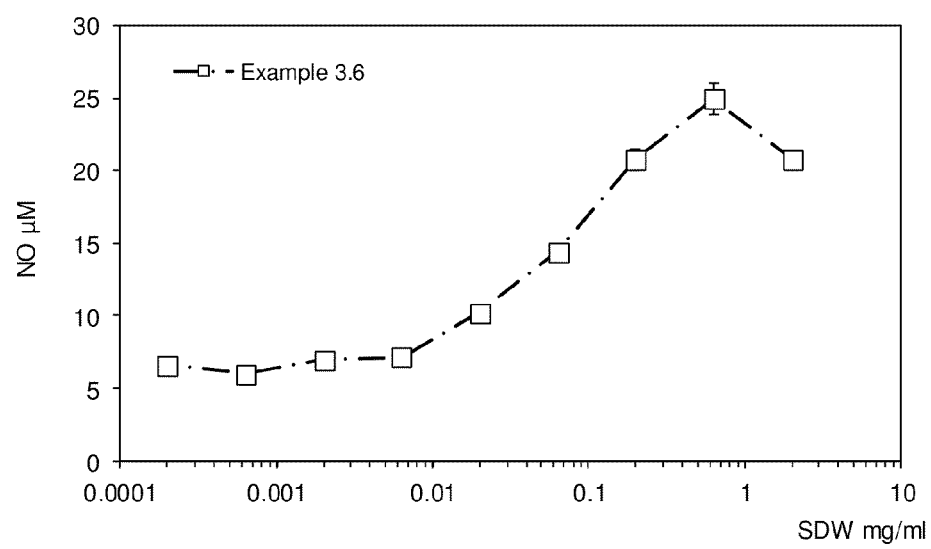
FIG. 5: Nitric oxide bioassay in murine macrophages of a purified mixture of *Diplococcus pneumonia* extracts (Example 3.6).
Figure 6:
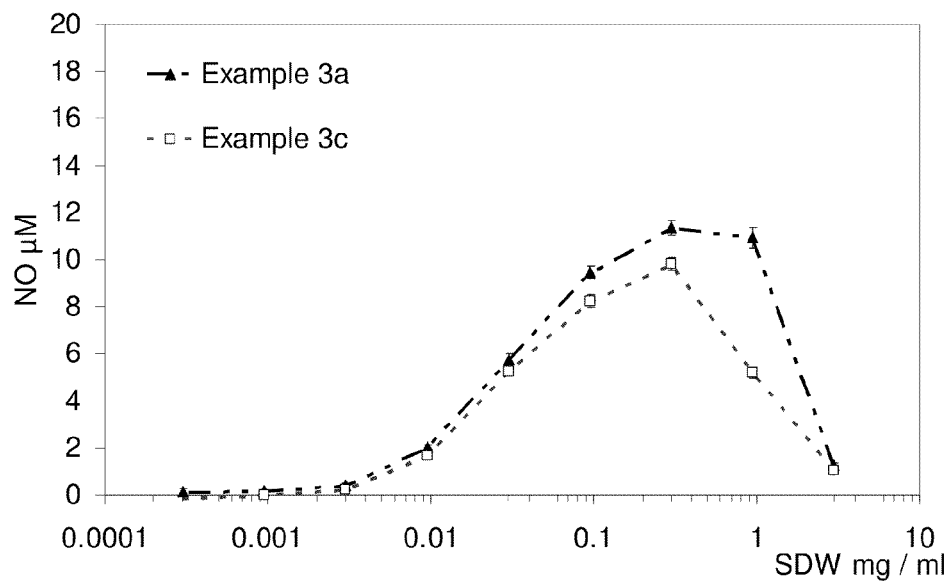
FIG. 6: Biological activities of the extracts of Example 3.1 and Example 3.3 (labeled 3a and 3c, respectively) in a nitric oxide bioassay in murine macrophages.
Figure 7:
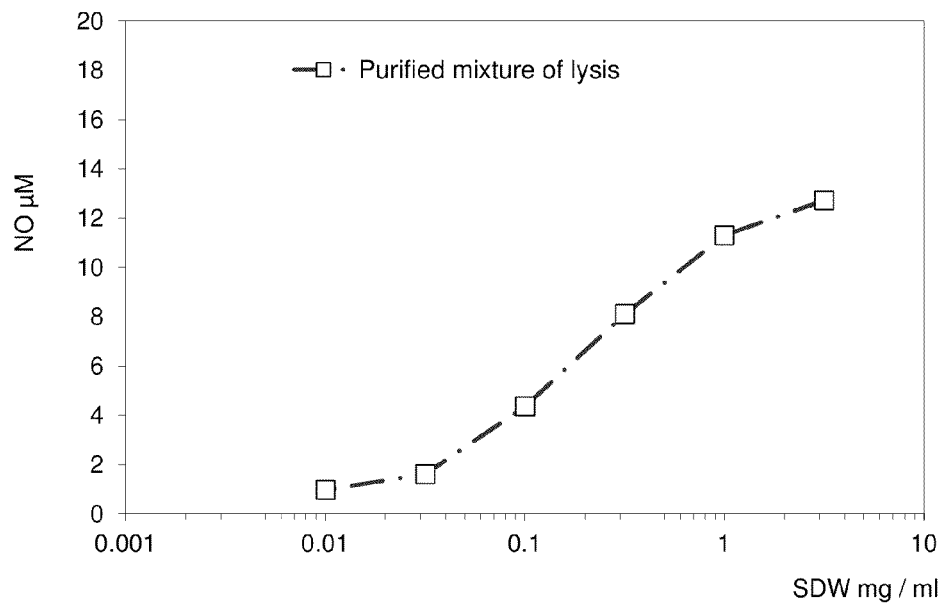
FIG. 7: Biological activities of a purified mixture of extracts from Examples 2.2, 3.6, 3.7, 3.8, 3.9, and 3.10 in a nitric oxide bioassay in murine macrophages.

Mortality was observed was daily in groups of 10 mice for 10 days. The results presented in FIG. 3 show that a 10 mg/mouse dose of the extract under the dosing conditions of this experiment could confer complete protection against reinfection. In contrast, only 70% of the control mice survived the influenza virus infection. Survival in the group receiving 1 mg/mouse of the drug was 70%.

Clinical Symptoms Observed in Treated Mice after Influenza Virus Infection

Groups of 10 mice each were observed daily for clinical symptoms of influenza virus infection. The clinical symptoms score is shown in the table below. Animals administered 10 mg dose of the extract showed mild clinical symptoms 2 days later and were apparently healthy earlier than the control group mice, indicating beneficial effect of higher dose. There were no significant differences in clinical scores between 1 mg dose-treated groups and controls.

controls, suggesting the effect of the extract was dose-dependent. Three days after the first infection, there were no significant differences in influenza hemagglutination-inhibition antibody levels between the treated groups and controls.

| Group | Days after Influenza virus infection | | | | | | | | | | | | | | | |
|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 |
| PBS | 0 | 0 | + | + | ++ | +++ | +++ | +++ | +++ | +++ | +++ | ++/+++ | ++/+++ | ++ | ++ | ++ |
| TTT 1 mg | 0 | 0 | + | + | ++ | ++ | +++ | +++ | +++ | +++ | +++ | +++ | ++/+++ | ++ | ++ | + |
| TTT 10 mg | 0 | 0 | 0 | 0 | + | +/++ | ++ | +++ | +++ | ++/+++ | ++/+++ | ++/+++ | +/+++ | ++ | ++ | 0 |

TTT = Treatment with Example 16 lysate
Only surviving animals were taken into consideration for the clinical symptoms score.
Code:
0: no ruffling of the fur, appeared healthy, and
+ to +++: progressive increase in ruffling of the fur; progressive decrease in movement and general activity.
Influenza hemagglutination inhibition antibody titers of treated mice Sera were collected on day 10 after influenza virus challenges, 3 mice per group, after the first and second infections. Sera obtained from immunized animals were stored at −20° C. All sera were pretreated with receptor-destroying enzyme to remove nonspecific inhibitors. Influenza hemagglutination-inhibition (HI) tests were performed in microtiter plates using 0.5% chicken red blood cells and 4 hemagglutinating units using standard procedures recommended by the World Health Organization (WHO, 2002). The results showing geometric mean HI antibody titers against influenza A/PR/8/34 (H1N1) virus are presented in the table below. There were no significant differences between the treated groups and controls after the first infection.

| Group | Titer D13 | *GMT | Titer D34 | *GMT |
|---|---|---|---|---|
| PBS | 320 | 403 | 640 | 640 |
| | 320 | | 640 | |
| | 640 | | 640 | |
| TTT 1 mg | 320 | 403 | 320 | 320 |
| | 320 | | 320 | |
| | 640 | | 320 | |
| TTT 10 mg | 320 | 320 | 640 | 1612 |
| | 320 | | 2560 | |
| | 320 | | 2560 | |

TTT = Treatment with Example 16
Sera were obtained 10 days after influenza virus challenge infection.
*Geometric mean titre Therefore, mice were given second (booster) challenge infection with A/PR/8/34 influenza virus 21 days after the first (primary) infection. The magnitude of antibody titers increased after challenge with A/PR/8/34 (H1N1) virus as shown above. Higher levels of HI antibody titers were observed with 10 mg/mouse dose of OM-85 BV. In contrast, 1 mg/mouse dose had lower antibody titers than 10 mg/mouse dose of the drug.

There were no significant differences between treated groups and controls in the lung virus detected. Nonetheless, clinical symptoms after aerosol infection with a mouse-pathogenic influenza A/PR/8/34 virus in animals administered 10 mg dose of an extract according to the invention occurred at least one complete day later than controls, and the experimental group also recovered apparently earlier than control mice. However, there were no significant differences in clinical scores between 1 mg dose treated groups and controls, suggesting the effect of the extract was dose-dependent. Three days after the first infection, there were no significant differences in influenza hemagglutination-inhibition antibody levels between the treated groups and controls.

However, upon second infection with A/PR/8/34 influenza virus three weeks after the first infection, a higher and significant magnitude of antibody induction was observed with 10 mg/mouse dose group.

This example shows that an extract according to the invention at the dosage of 10 mg per mouse was capable of conferring protection against mouse-pathogenic aerosol influenza A/PR/8/34 (H1N1) virus infection as determined by multiple parameters. Embodiments of the invention may therefore activate in vivo an immune response against a virus. Since the extracts may be, in some embodiments, manufactured exclusively from pathogenic bacteria, as was the extract tested in this example, this suggests that embodiments of the invention may activate the innate immune system.

Example 7

Activity of Embodiments of the Invention in a Murine Nitric Oxide Test

Six-week old male C57/BL6 mice (six weeks old male, SPF quality, Charles Rivier, FR) were killed by $CO_2$ inhalation. The hip, femur, and tibia from the posterior appendage were removed. The bone marrow was extracted from the lumen by injecting Dulbecco's Modified Eagle Medium (DH) through the bone after cutting both end portions. After washing, the stem cells were resuspended (40,000 cells/mL) in DH medium supplemented with 20% horse serum and 30% L929 cell supernatant. The cell suspension was incubated for 8 days in an incubator at 37° C. under 8% $CO_2$ and moisture-saturated atmosphere. Macrophages were then detached with ice-cold PBS, washed and resuspended in DH medium supplemented with 5% fetal calf serum (FCS), amino acids and antibiotics (DHE medium). The cell density was adjusted to 700,000 cells/mL. Aqueous solutions of the products were serially diluted in DHE medium directly in microtiter plates. The products were tested in triplicates and each microtiter plate comprised a negative control composed of medium. The final volume in each well was 100 μL. 100 μL of the cell suspension was added to the diluted products and the cells were incubated for 22 h in an incubator at 37° C., under 8% CO2 and a moisture-saturated atmosphere. At the end of the incubation period, 100 μL of supernatant was transferred to another microtiter plate and the nitrite concentration produced in each supernatant was determined by running a Griess reaction. 100 µL of Griess reagent (5 mg/mL of sulfanilamide+0.5 mg/mL of N-(1-naphtyl)ethylene-diamine hydrochloride) in 2.5% aqueous phosphoric acid was added to each well. The microtiter plates were read with a spectrophotometer (SpectraMax Plus, Molecular Devices) at 562 nm against a reference at 690 nm. The nitrite concentration was proportional to nitric oxide content being formed. The nitrite content was determined based on a standard curve. The results were given in µM nitric oxide (NO) as mean value±standard deviation and plotted as a dose response curve (See FIGS. 4-7).

Example 8

Limulus Amoebocyte Lysate Chromogenic (LAL) Test

To determine the presence of endotoxin-like molecules, an LAL test was performed with the Chromogenic—LAL Kit of Bio-Whittaker.

This test is based on activation by lipopolysaccharide (LPS) or products of comparable structure, by an enzymatic cascade present in the LAL. This enzymatic activation is demonstrated by the splitting of a chromogen linked to a peptide by a protease. The enzymatic reaction is carried out at 37° C. and the formation of the chromogen over time is measured at 405 nm. The time necessary to reach 0.2 units of D.O. is recorded and the endotoxic activity calculated in relation to a LPS standard (standard curve).

The results of such an example experiment on extracts according to the invention are expressed in the table below in EU (Endotoxin Unit) in relation to a standardized preparation of *E. coli* LPS (1 EU corresponds to 0.09 ng equivalent LPS).

| Conditions of lysis (Time of lysis, amount of Starting Material, initial percentage of NaOH) | EU/ml | ng equivalent LPS/ml |
|---|---|---|
| Hemo NaOH 1% 100 g/l/T 22 h | 169900 ± 600 | 15291 |
| Hemo NaOH 1% 125 g/l/T 211 h | 2811000 ± 82644 | 252990 |
| Hemo NaOH 1% 50 g/l/T 211 h | 33950 ± 224 | 3055 |
| Hemo NaOH 1% 50 g/l/T 22 h | >5000000 | 450000 |
| Hemo NaOH 1% 50 g/l/T 92 h | >500000 | 45000 |
| Hemo NaOH 2% 25 g/l/T 92 h | 65430 ± 565 | 5888 |
| Hemo NaOH 2% 50 g/l/T 211 h | 23560 ± 142 | 2120 |
| Hemo NaOH 2% 50 g/l/T 22 h | 579200 ± 1062 | 52128 |
| Hemo NaOH 2% 50 g/l/T 92 h | 7927 ± 320 | 713 |
| Hemo NaOH 3% 125 g/l/T 211 h | 30000 ± 113 | 2700 |
| Hemo NaOH 3% 25 g/l/T 22 h | 6883 ± 34 | 619 |
| Hemo NaOH 3% 50 g/l/T 22 h | 10690 ± 41 | 962 |
| Hemo NaOH 4% 100 g/l/T 92 h | 11380 ± 36 | 1024 |
| Hemo NaOH 4% 12.5 g/l/T 22 h | 3415 ± 40 | 307 |
| Hemo NaOH 4% 12.5 g/l/T 92 h | 10500 ± 37 | 945 |
| Hemo NaOH 10% 100 g/l/T 92 h | 1229 ± 38 | 110 |
| Hemo NaOH 10% 12.5 g/l/T 211 h | 224 ± 17 | 20 |
| Hemo NaOH 10% 125 g/l/T211 h | 602 ± 6 | 54 |
| Example 4 | 20140 | 1812 |
| Example 3.15 | 108 ± 0.5 | 10 |
| $H_2O$ | <0.005 | 15291 |

Example 9

Inhibition of Histamine Secretion

An in vitro rat model of mast cell degranulation (proposed by the CRO CEREP, catalog number 2006: 771-c, ref Håkanson R, Rönnberg A L, Sjölund K. *Anal Biochem*, 1972 Jun 47(2):356-70) was employed to investigate the way in which an embodiment of the invention (comprising 21 bacterial strains) would inhibit histamine secretion by compound 48/80-stimulated mastocytes. The protocol and experimental conditions are briefly summarized in the tables below:

Protocol

| Assay | Origin | Reference Compound | Reference |
|---|---|---|---|
| Histamine secretion (compound 48/80-stimulated) | rat mast cells | SCG | Hakanson et al. (1972) |

Experimental Conditions

| Assay | Stimulus | Incubation | Reaction Product | Method of Detection |
|---|---|---|---|---|
| Histamine secretion (compound 48/80-stimulated) | Compound 48/80 (0.1 µg/ml) | 2 min./ 37° C. | histamine | Fluorimetry |

Analysis and Expression of the Results

The results are expressed as a percent of control specific activity: (measured specific activity/control specific activity)×100, obtained in the presence of the test compounds. The IC50 values (concentration causing a half-maximal inhibition of control specific activity) were determined by non-linear regression analysis of the inhibition curves generated with mean replicate values using Hill equation curve fitting (Y=D+[(A−D)/(1+(C/C50)nH)], where Y=specific activity, D=minimum specific activity, A=maximum specific activity, C=compound concentration, C50=IC50, and nH=slope factor). This analysis was performed using software developed at Cerep (Hill software) and validated by comparison with data generated by the commercial software SigmaPlot® 4.0 for Windows® (© 1997 by SPSS Inc.).

In each experiment, the reference was tested concurrently with the test extract in order to assess the assay suitability. Several concentrations were tested (for $IC_{50}$ value determination), and the data were compared with historical values determined at Cerep. The assay was considered valid if the suitability criteria were met, in accordance with the corresponding standard operating procedure. The $IC_{50}$ values determined for the test extract and the reference (measured twice) are indicated in the table below. The $IC_{50}$ values for the reference were within accepted limits of the historic average ±0.5 log units.

Figure 8:
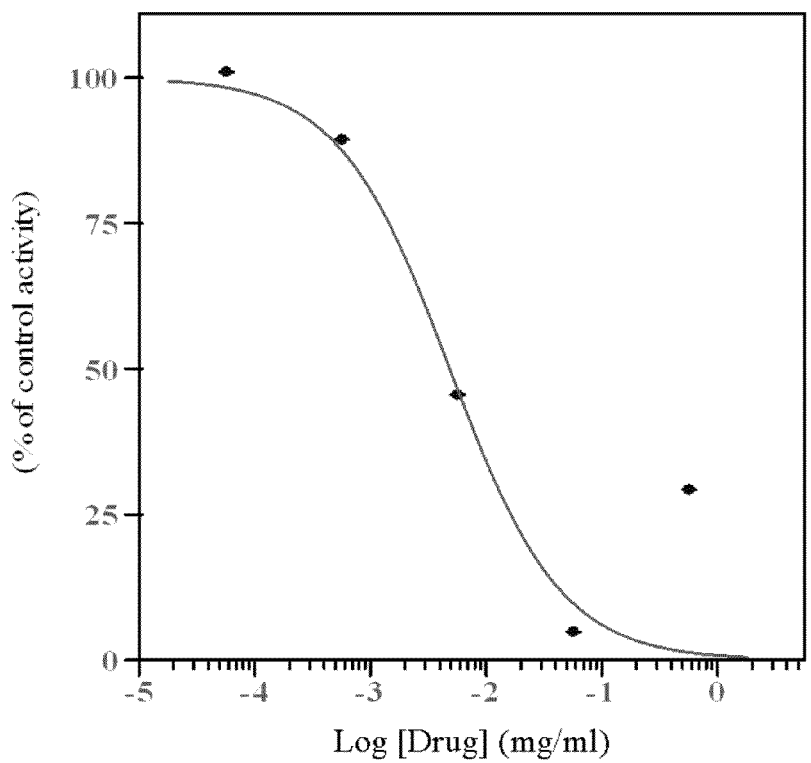
FIG. 8: Effects of an extract according to the invention on the secretion of histamine from compound 48/80-stimulated rat mast cells.

The corresponding inhibition curves obtained with the test extract are shown in FIG. 8.

| Compounds tested | $IC_{50}$ |
|---|---|
| Test Extract | 0.0049 mg/ml |
| SCG (reference 1) | 4.7E−06M |
| SCG (reference 2) | 1.1E−06M |

The results indicate that the tested extract is a potential inhibitor of histamine secretion induced by compound 48/80-stimulated mast cells.

Example 10

Effect of an Embodiment of the Invention in an *Escherichia coli* Infection Model in an LPS-Insensitive Strain of Mice An embodiment of the invention was tested in a recognized in vivo model of *E. coli* bacterial infections (See Hopkins et al., Inheritance of susceptibility to induced *Escherichia coli* bladder and kidney infections in female C3H/HeJ mice., *J Infect Dis*. 2003 Feb. 1; 187(3):418-23.). C3H/HeJ mice were mutated for the toll-like receptor gene (TLR4), and are insensitive to TLR4 agonists such as LPS. Therefore this model is suitable to detect the effects of drugs acting via other routes than TLR4.

One group of 10-12 weeks old female C3H/HeJ mice (8 mice) was treated orally with an extract similar to that of Example 3.15 for 10 days prior to *E. coli* infection.

The animals were maintained under normal conditions at ambient temperature of 18-26° C. and a relative humidity of 30 to 70%. The light program was set on a light-dark cycle of 12:12 hours.

Animals were fed a standard diet provided by Harlan Sprague Dawley (Indianapolis, Ind.) laboratories. Tap water was provided ad libitum, unless when indicated elsewhere.

Treated animals received orally 143 mg of lyophilizate (i.e. 25 mg (17.5%) of bacterial extract and 118 mg (82.5%) of excipients) per animal per administration of the extract.

Inoculation

Mice were inoculated intravesically with PBS or with uropathogenic *E. coli*, according to a minimal inoculum protocol that greatly reduces the likelihood of reflux-associated inoculation of the kidneys and induces infections in all animals inoculated. The *E. coli* strain 1677, isolated from the urine of a woman with a febrile UTI, was used in these experiments. To prepare the inoculum, bacteria were grown from frozen stock by 2 passages in tryptose broth (Difco Laboratories), washed with PBS, and resuspended to a concentration of $2 \times 10^{10}$ bacteria/mL. Mice were deprived of water for 1 h and had urine expressed from their bladders immediately before inoculation. Ten microliters of bacterial inoculum were instilled into the bladder by urethral catheterization under isoflurane anesthesia, resulting in a dose of $2 \times 10^8$ *E. coli* per mouse. The animals were allowed to recover from anesthesia and water was given back 1 h later.

Mice were killed 10 days after inoculation to assess the intensities of bladder and kidney infections. The bladder and both kidneys of each animal were removed, weighed, and homogenized in sterile PBS, after which the homogenates were serially plated onto Levine's eosin-methylene blue agar (Difco Laboratories). The number of *E. coli* colonies on each plate was counted after overnight incubation at 37° C. and was used to calculate the total number of bacteria in each bladder or pair of kidneys.

Fisher's protected least significant difference test was used to determine the statistically significant differences between the mean total colony-forming unit (CFU) values for different groups of mice (PBS, Untreated infected group, and Treated and infected group). The bladder and kidney infection data was transformed using total CFU=log 10 [(CFU+100)/mg tissue], where CFU was the total number of colony-forming units calculated per tissue sample.

Figure 9A:
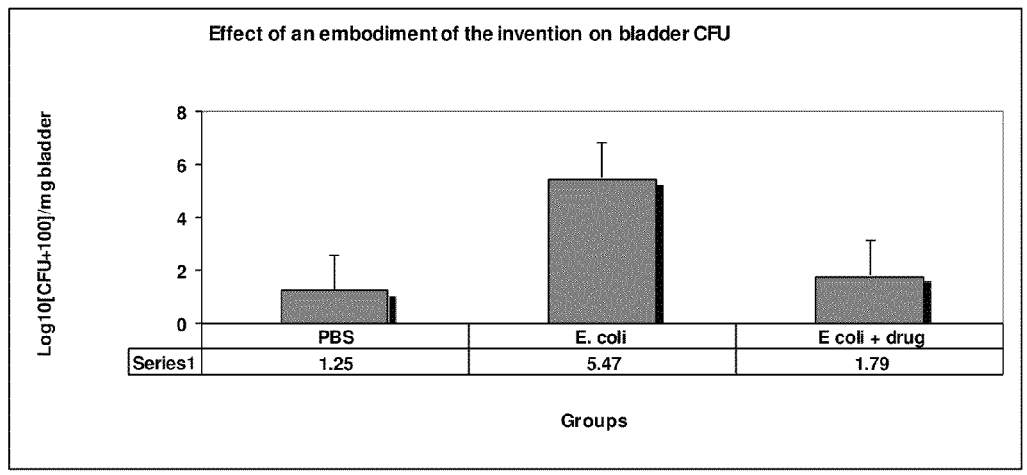
FIG. 9: Mean total colony-forming unit (CFU) values in (a) bladder, and (b) kidney tissues for different experimental groups.
Figure 9B:
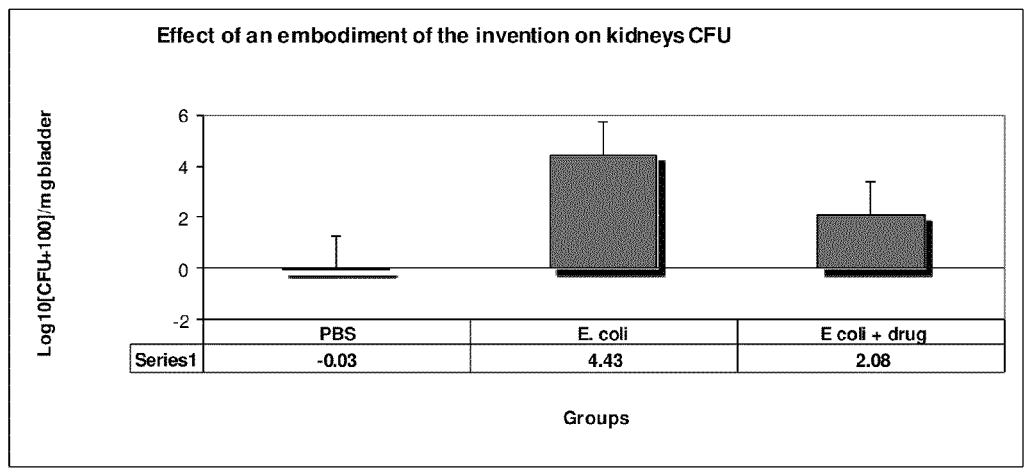

The results obtained are shown in FIGS. 9a and 9b for bladder and kidneys, respectively. Mice were sacrificed 10 days after inoculation to assess the intensities of bladder and kidney infections. The bladder and both kidneys of each animal were removed, weighed, and homogenized in sterile PBS, after which the homogenates were serially plated onto Levine's eosin-methylene blue agar (Difco Laboratories). The number of *E. coli* colonies on each plate was counted after overnight incubation at 37° C., and after the addition of 100 CFU to the results obtained, the sum obtained in each case was divided by the mg of tissues (i.e. total CFU=log 10 [(CFU+100)/mg tissue] in order to calculate the mean total number of bacteria+/−SEM for bladders or kidneys. The bacterial extract decreased by a factor >3 (bladder) and >2 (kidneys) the logarithmic values obtained, suggesting that the number of colonies cultured from the bladder and the kidneys was decreased by at least a factor of 1000 and 100, respectively. These results demonstrate the immunological activity of an embodiment of the invention.

Example 11

Effect of the an Embodiment of the Invention in a Murine Model of Intraperitoneal *Salmonella typhimurium* Infection in C57/bl Mice An embodiment of the invention was also tested in a murine model of intraperitoneal *Salmonella typhimurim* infection. C57BL/6 mice were kept for 7 days before oral treatment. Treated animals received 85 mg of lyophilizate (i.e. 15 mg (17.5%) of bacterial extract and 70 mg (82.5%) of excipients) per animal per administration. The experiment consisted of one experimental group of 20 mice treated with an extract similar to that of Example 3.15, and a control group of 20 mice treated with a water control. For treatment, the extract was dissolved daily in distilled water in order to have a single dose in a final volume of 0.5 ml. This 0.5 ml volume was given to each mouse orally once a day for 10 consequent days before all mice were challenged intraperitonally with *Salmonella typhimurium* strain 415 (I. Mechnokov Institute for Vaccines and Sera, Russian Academy of Medical Sciences).

The extract was introduced in a single dose of 85 mg per mouse (i.e. 15 mg of active principle with 82.5% of excipents). Mice in the control group received a sham treatment using oral administration of 0.5 ml water daily for 10 days. A preliminary dose-finding challenge ranged from 102 to 105 CFU of Salmonellae per mouse. The dose of 104 CFU was selected the main experiment because this dose provided approximately 50% of survivors in untreated animals.

After the challenge, mice were kept under the standard conditions for laboratory animals. Daily observation and records of death were performed during a period of 21 days post-infection. The anti-infective efficacy of the extract (see tables below) was estimated according to the post-infection survival rate (SR), and the post-infection average duration of life (ADL), and the defense factor (DF), and the preparation efficacy index (EI), which were calculated for each experimental group. The SR was taken as a percent of live animals in the experimental group on day 21 post-infection.

The ADL, DF and EI were calculated using the following formulas:

$$ADL = (X1 + x2 + \ldots + Xn) : N,$$

where ADL is an average duration of life, X1 to Xn are durations of life post-infection for experimental mice #1 to #n, and N—is a total number of animals in the experimental group.

$$DF = CD : ED,$$

where DF is the defense factor, CD is a percent of death in the control group, and ED is a percent of death in the experimental group.

EI=[(DF−1):DF]×100%, where EI is the preparation efficacy index and DF is the defense factor.

| Death records in control and experimental group during the period of 21 days post-infection with $10^4$ CFU of *Salmonella typhimurium*. | | | | | | | | | | | | | | | | | | | | | | | |
|---|---|---|---|---|---|---|---|---|---|---|---|---|---|---|---|---|---|---|---|---|---|---|---|
| Pre-treatment | Nr of mice before challenge | Number of dead mice from day 1 to day 21 post infection | | | | | | | | | | | | | | | | | | | | | Survival Rate (%) |
| | | 1 | 2 | 3 | 4 | 5 | 6 | 7 | 8 | 9 | 10 | 11 | 12 | 13 | 14 | 15 | 16 | 17 | 18 | 19 | 20 | 21 | |
| $H_2O$ | 19 | — | — | — | 1 | 2 | 2 | — | 1 | — | — | — | 1 | — | 1 | — | — | — | — | — | — | — | 58 |
| Example 3.15 | 19 | — | — | — | — | — | — | — | — | — | — | — | — | — | — | — | — | — | — | — | — | — | 100 |

| Defense efficacy of Example 3.15 in the model of *Salmonella thyphimurium* lethal infection in C57BL/6 mice. | | | | | |
|---|---|---|---|---|---|
| Pre-Treatment With Substances | Death Rate (%) | Survival Rate (%) | ADL (days) | DF | EI (%) |
| $H_2O$ | 42 | 58 | 15.3 | 1 | 0 |
| Example 3.15 | 0 | 100 | 21 | Maximum defense | 100 |

During the experiment it was evident that the extract appeared well tolerated. In the control group of mice pre-treated with water, the survival rate during the period of observation (21d) was 58%, and the ADL occurred to be 15.3 days. In contrast, all the mice that received the extract according to this invention survived to the challenge. These results suggest that embodiments of the Invention could be beneficial against certain bacterial infections in human beings.

Example 12

Effect of an Embodiment of the Invention on Production of Regulatory T Cells in Mucosal Trachea During an Allergen Challenge The immuno-regulatory potential of an embodiment of the invention in a model of acute allergic inflammation was tested. The experiment was performed to determine if, in PVG rats, administration of the an extract according to the invention would increase the pool size of available mucosal-homing T regulatory (Treg) cells, resulting in increased numbers of Tregs in airway mucosal tissues during episodic inflammation.

Inbred PVG rats were bred and maintained free of common rat pathogens. Randomly selected animals of both sexes aged 8-13 weeks were utilized throughout.

The daily consecutive feeds (gavage) were performed with 400 ug of lyophilizate provided/g of body (or 400 mg/kg/day). Treg populations in airway tissue of PVG rats were phenotypically identified in the study groups. Phenotypic characterisation of rat tracheal tissue required group sizes of 5 to 10 animals pooled to yield sufficient cells for the analyses. Tracheal tissues were digested in Collagenase/DNase to yield single cell suspensions followed by flow cytometric analysis of surface expression of CD4, CD25, Foxp3, and TCRαβ. First, animals were sensitised with OVA on day zero (d0) and fed with an extract similar to that of Example 3.15 or placebo from d10 to d17; on d18 they were challenged with aerosolised OVA and resulting Th cell/Treg (FoxP3) response measured 24 hrs later. For intracellular staining of Fox p3, anti-mouse/rat FoxP3-FLR staining kit from eBioscience (San Diego, Calif.) was used as described by the manufacturer. Data were acquired on a FACSCalibur flow cytometer (BD Biosciences) and analysed using Flowjo software (version 4.6.1, Tree Star Inc). OVA was from Sigma Chemicals Co. (St Louis, Mo.).

Figure 10A:
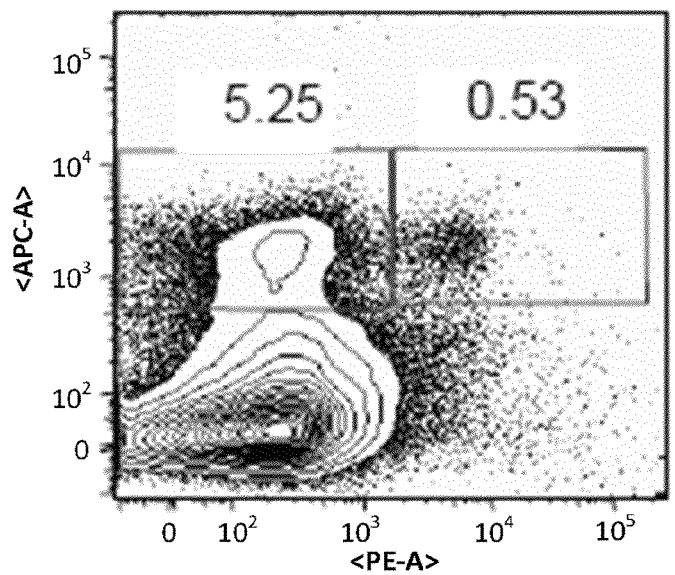
FIGS. 10A-10D: Effect of an embodiment of the invention in an *Escherichia coli* infection model in an LPS-insensitive strain of mice. The figure shows flux cytometry data with (a) markers CD4 vs FoxP3, and (b) TCR vs FoxP3.
Figure 10B:
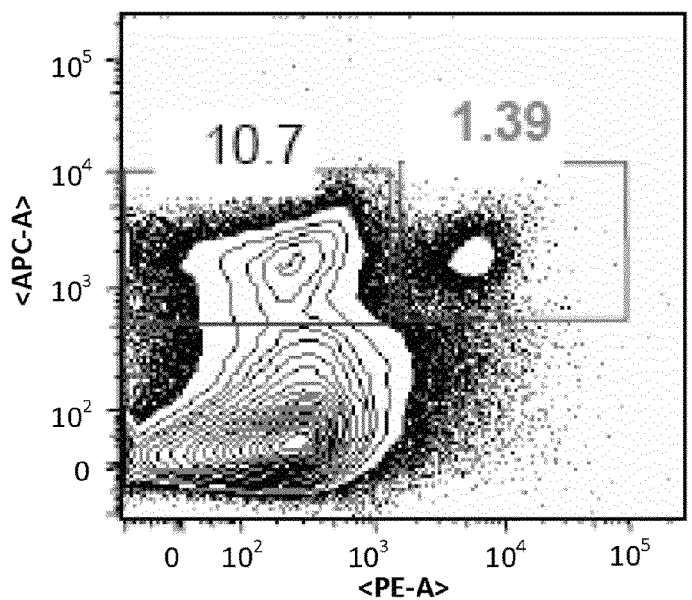
Figure 10C:
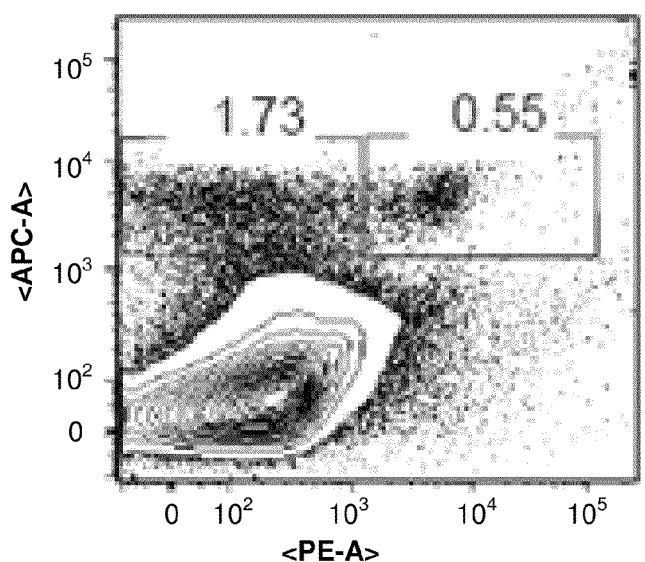
Figure 10D:
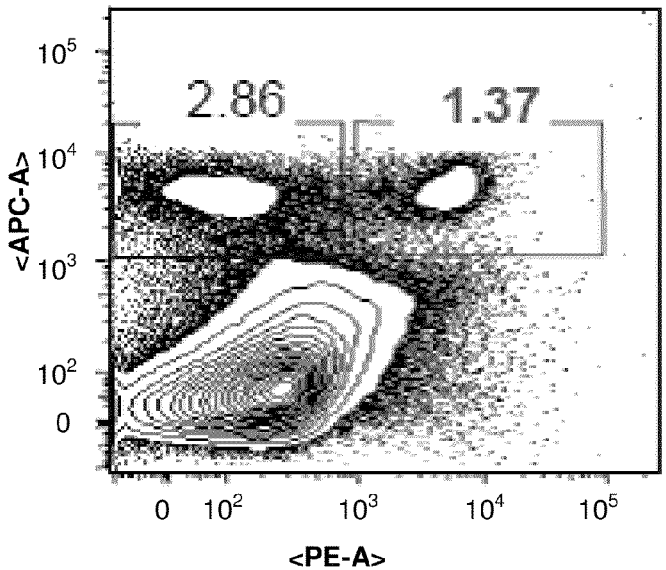

FIGS. 10A-10D show original flux cytometry data (in FIG. 10A and 10B, the markers were CD4 vs FoxP3, and in FIG. 10C and 10D, the markers were TCR vs FoxP3). The cells were obtained from airway mucosa after in OVA sentisized rats (i.p. on day 0) and 24 hours after aerosol OVA challenge (day 18). FIGS. 10B and 10D show that when the animals were dosed orally from day 10 to day 18 with the extract, there was an increased percentage of FoxP3 positive CD4 cells (and TCR respectively) when compared to controls shown in FIGS. 10A and 10C (untreated animals sensitized with OVA and OVA challenged animals).

This example shows that embodiments of the invention may have therapeutic value in case of inflammatory allergic crisis.

Additional Examples Include

An extract from one or more bacterial species chosen from: *Moraxella catarrhalis, Haemophilus influenzae, Klebsiella pneumoniae, Staphylococcus aureus, Streptococcus pneumoniae, Streptococcus pyogenes, Streptococcus sanguinis, Staphylococcus Hemolyticus, Enterococcus faecalis, Streptococcus mutans, Streptococcus anginosus, Streptococcus mitis, Streptococcus salivarius, Neisseria sicca, Haemophilus parainfluenzae, Actinobacillus (Hemophilus) actinomycetemcomitans*, and *Eikenella corrodens*, wherein, during preparation of said extract, the one or more bacterial strains are lysed at a pH of greater than 12, and the extract is treated so as to remove nucleic acids; and wherein the extract does not pose a risk of prion diseases upon administration to a patient.

The extract of the preceding paragraph obtained from at least one strain of each of the following bacterial species: *Moraxella catarrhalis, Haemophilus influenzae, Klebsiella pneumoniae, Staphylococcus aureus, Streptococcus pneumoniae, Streptococcus pyogenes, Streptococcus sanguinis, Staphylococcus Hemolyticus, Enterococcus faecalis, Streptococcus mutans, Streptococcus anginosus, Streptococcus mitis, Streptococcus salivarius, Neisseria sicca, Haemophi-* lus parainfluenzae, Actinobacillus (Hemophilus) actinomycetemcomitans, and Eikenella corrodens.

The extract of the preceding paragraph obtained from each of the following bacterial strains: Moraxella (Moraxella) catarrhalis 3622, Moraxella (Moraxella) catarrhalis 3625, Moraxella (Moraxella) catarrhalis I-045, Haemophilus influenzae 8467, Klebsiella pneumoniae ssp. ozaenae 5050, Klebsiella pneumoniae ssp. pneumoniae 204, Klebsiella pneumoniae ssp. pneumoniae 5056, Staphylococcus aureus I-049, Staphylococcus aureus I-050, Staphylococcus aureus I-051, Staphylococcus aureus I-052, Staphylococcus aureus I-053, Staphylococcus aureus I-054, Streptococcus pneumoniae 7465, Streptococcus pneumoniae 7466, Streptococcus pneumoniae 7978, Streptococcus pneumoniae 10319, Streptococcus pyogenes 8191, Streptococcus sanguinis I-046, Streptococcus sanguinis I-047, Streptococcus sanguinis I-048, Staphylococcus Hemolyticus 11042, Enterococcus faecalis 103015, Streptococcus mutans 10449, Streptococcus anginosus 10713, Streptococcus mitis 12261, Streptococcus salivarius 102503, Neisseria sicca 103345, Haemophilus parainfluenzae 7857, Actinobacillus (Hemophilus) actinomycetemcomitans 52.105, and Eikenella corrodens 10596.

The extract of any of the three preceding paragraphs, wherein the extract comprises less than 100 µg/mL nucleic acid.

The extract of any of the three preceding paragraphs, wherein the extract comprises at least 0.3 mg/mL of saccharides.

The extract of any of the three preceding paragraphs, wherein the extract comprises between 0.3 and 4.5 mg/mL of saccharides.

The extract of any of the preceding paragraphs, wherein at least one saccharide is selected from the group consisting of monosaccharides, disaccharides, and polysaccharides.

The extract of the preceding paragraph, wherein at least one polysaccharide is a branched polysaccharide.

The extract of any of the preceding paragraphs, wherein at least one saccharide is chemically modified.

The extract of any of the preceding paragraphs, wherein the extract comprises between 1.5 to 2.5 mg/mL of free amino acids.

The extract of any of the paragraphs above, wherein lysis is performed at a pH of 12.6 to 13.4.

The extract of any of the preceding paragraphs, wherein the extract is treated so as to remove particulate and/or insoluble components.

The extract of any of the preceding paragraphs, wherein each bacterial strain is cultured in a medium that does not pose a risk of prion diseases.

The extract of any of the preceding paragraphs, wherein at least one amino acid chosen from aspartic acid, glutamic acid, serine, histidine, alanine, arginine, tyrosine, methionine, phenylalanine, and lysine is racemized by at least 10%.

The extract of any of the preceding paragraphs, wherein the free amino acids of the extract comprise between 1 and 80% D-amino acids.

The extract of any of the preceding paragraphs, wherein the free amino acids of the extract comprise between 10 and 45% D-amino acids.

The extract of the preceding paragraph, wherein the free amino acids of the extract comprise between 25 and 35% D-amino acids.

The extract of any of the preceding paragraphs, wherein the extract comprises at least one D-amino acid chosen from D-aspartic acid and D-asparagine, D-glutamic acid and D-glutamine, D-serine, D-methionine, D-histidine, D-alanine, D-arginine, D-phenylalanine, D-tyrosine, D-leucine, D-lysine, D-valine, and D-threonine.

The extract of the preceding paragraph, wherein the concentration of any one D-amino acid comprises between 1 and 50% of the free amino acid concentration.

The extract of the preceding paragraph, wherein the concentration of any one D-amino acid comprises between 10 and 40% of the free amino acid concentration.

The extract of the preceding paragraph, wherein the concentration of any one D-amino acid comprises between 15 and 35% of the free amino acid concentration.

The extract of any of the preceding paragraphs, wherein the extract comprises between 6 and 75 mg/mL of one or more proteins.

The extract of the preceding paragraph, wherein the extract comprises between 6 and 8 mg/mL of one or more proteins.

The extract of any of the preceding paragraphs, wherein the one or more proteins have molecular weights of less than 30 kDa.

The extract of any of the preceding paragraphs, wherein the one or more proteins have molecular weights of less than 10 kDa.

The extract of any of the preceding paragraphs, wherein the survival rate of at least 8 mice with wild-type LPS sensitivity 13 days after challenge with Salmonella thyphimurium is at least 70%, wherein the dose of Salmonella thyphimurium is chosen such that the survival rate of at least 8 control mice is 60% or lower.

The extract of the preceding paragraph, wherein the survival rate is at least 80%.

The extract of the preceding paragraph, wherein the survival rate is at least 90%.

The extract of any of the preceding paragraphs, wherein the extract comprises less than 5000 ng of LPS equivalents according to a limulus amoebocyte lysate (LAL) chromogenic test.

A pharmaceutical composition comprising the extract of any of the above paragraphs.

A method of treating a subject suffering from or at risk of developing a respiratory disorder, comprising administering an effective amount of any of the extracts of the above paragraphs to said subject.

The method of the preceding paragraph, wherein the subject is a human or domestic mammal.

The method of either of the two preceding paragraphs, wherein the respiratory disorder or allergic condition is upper and lower respiratory infections, atopic dermatitis, nasopharyngitis, sinusitis, pharyngitis, tonsillitis, laryngitis, tracheitis, laryngopharyngitis, influenza, pneumonia, bronchopneumonia, bronchitis, lower respiratory infections, allergic rhinitis, allergic asthma, rhinitis, nasopharyngitis, pharyngitis, sinusitis, tonsillitis, laryngitis, laryngotracheitis, bronchitis, obstructive pulmonary disease with acute lower respiratory infection, or obstructive pulmonary disease with acute exacerbation.

A process for preparing an extract obtained from one or more bacterial species chosen from: Moraxella catarrhalis, Haemophilus influenzae, Klebsiella pneumoniae, Staphylococcus aureus, Streptococcus pneumoniae, Streptococcus pyogenes, Streptococcus sanguinis, Staphylococcus Hemolyticus, Enterococcus faecalis, Streptococcus mutans, Streptococcus anginosus, Streptococcus mitis, Streptococcus salivarius, Neisseria sicca, Haemophilus parainfluenzae, Actinobacillus (Hemophilus) actinomycetemcomitans, and Eikenella corrodens, comprising:

(a) culturing each bacterial strain in a medium that does not pose a risk of prion diseases;
(b) lysing each strain at an initial pH of greater than 12; and
(c) passing the product of (b) at least once through a microfilter and at least once through an ultrafilter.

The process of the preceding paragraph, wherein the extract is obtained from at least one strain of each of the following bacterial species: *Moraxella catarrhalis, Haemophilus influenzae, Klebsiella pneumoniae, Staphylococcus aureus, Streptococcus pneumoniae, Streptococcus pyogenes, Streptococcus sanguinis, Staphylococcus Hemolyticus, Enterococcus faecalis, Streptococcus mutans, Streptococcus anginosus, Streptococcus mitis, Streptococcus salivarius, Neisseria sicca, Haemophilus parainfluenzae, Actinobacillus (Hemophilus) actinomycetemcomitans*, and *Eikenella corrodens*.

The process of the preceding paragraph, wherein the extract is obtained from each of the following bacterial strains: *Moraxella (Moraxella) catarrhalis* 3622, *Moraxella (Moraxella) catarrhalis* 3625, *Moraxella (Moraxella) catarrhalis* I-045, *Haemophilus influenzae* 8467, *Klebsiella pneumoniae* ssp. *ozaenae* 5050, *Klebsiella pneumoniae* 204, *Klebsiella pneumoniae* 5056, *Staphylococcus aureus* I-049, *Staphylococcus aureus* I-050, *Staphylococcus aureus* I-051, *Staphylococcus aureus* I-052, *Staphylococcus aureus* I-053, *Staphylococcus aureus* 1-054, *Streptococcus pneumoniae* 7465, *Streptococcus pneumoniae* 7466, *Streptococcus pneumoniae* 7978, *Streptococcus pneumoniae* 10319, *Streptococcus pyogenes* 8191, *Streptococcus sanguinis* I-046, *Streptococcus sanguinis* I-047, *Streptococcus sanguinis* I-048, *Staphylococcus Hemolyticus* 11042, *Enterococcus faecalis* 103015, *Streptococcus mutans* 10449, *Streptococcus anginosus* 10713, *Streptococcus mitis* 12261, *Streptococcus salivarius* 102503, *Neisseria sicca* 103345, *Haemophilus parainfluenzae* 7857, *Actinobacillus (Hemophilus) actinomycetemcomitans* 52.105, and *Eikenella corrodens* 10596.

The process of any of the preceding paragraphs, wherein the lysis is carried out at an initial pH of greater than 12.5.

The process of any of the preceding paragraphs, wherein the lysis is carried out at an initial pH of 12.6 to 13.4.

The process of any of the preceding paragraphs, wherein the lysis is carried out for a period of from 40 hours to 10 days at a temperature of 30-60° C.

The process of any of the preceding paragraphs, wherein the microfilter is 0.45 microns and the ultrafilter is 30 KDa.

The process of any of the preceding paragraphs, wherein part (c) comprises tangential flow filtration.

The process of the preceding paragraph, wherein the tangential flow filtration is carried out for 5 to 15 cycles.

The process of any of the preceding paragraphs, further comprising passing the product of (c) through a second microfilter at 0.2 microns.

The process of any of the preceding paragraphs, wherein part (b) is carried out with 10-120 g/l bacterial dry weight of material.

The process of any of the preceding paragraphs, wherein the tangential flow filtration is performed as set forth in FIG. 1.

The process of any of the preceding paragraphs, wherein the tangential flow filtration is performed as set forth in FIG. 1, in serpentine mode.

A product obtained by any of the processes of the preceding paragraphs.

A method of treating a subject suffering from or at risk of developing a respiratory disorder, comprising administering an effective amount of any of the product of any one of the processes of the above paragraphs to said subject.

The method of the preceding paragraph, wherein the subject is a human or domestic mammal.

What is claimed is:

1. An extract which preserves and/or retains saccharide components from one or more bacterial species chosen from *Moraxella catarrhalis, Haemophilus influenzae, Klebsiella pneumoniae, Staphylococcus aureus, Streptococcus pneumoniae, Streptococcus pyogenes*, and *Streptococcus sanguinis*, wherein, during preparation of said extract, the one or more bacterial species are lysed at a pH of greater than 12, wherein said extract is treated so as to remove nucleic acids to less than 100 µg/ml, wherein one or more amino acids of the proteins of said extract are racemized from L to D, said one or more amino acids being chosen from aspartic acid, asparagine, glutamic acid, glutamine, serine, methionine, histidine, alanine, arginine, phenylalanine, tyrosine, leucine, lysine, valine, and threonine, wherein the extract comprises between 6 and 8 mg/mL of one or more proteins, wherein said one or more proteins has a molecular weight of less than 10 kDa.

2. The extract of claim 1 obtained from each of the following bacterial strains: *Moraxella catarrhalis* 3622, *Moraxella catarrhalis* 3625, *Moraxella catarrhalis* I-045, *Haemophilus influenzae* 8467, *Klebsiella pneumoniae* ssp. *ozaenae* 5050, *Klebsiella pneumoniae* ssp. *pneumoniae* 204, *Klebsiella pneumoniae* ssp. *pneumoniae* 5056, *Staphylococcus aureus* I-049, *Staphylococcus aureus* I-050, *Staphylococcus aureus* I-051, *Staphylococcus aureus* I-052, *Staphylococcus aureus* I-053, *Staphylococcus aureus* I-054, *Streptococcus pneumoniae* 7465, *Streptococcus pneumoniae* 7466, *Streptococcus pneumoniae* 7978, *Streptococcus pneumoniae* 10319, *Streptococcus pyogenes* 8191, *Streptococcus sanguinis* I-046, *Streptococcus sanguinis* I-047, and *Streptococcus sanguinis* I-048.

3. The extract of claim 1, wherein the extract comprises between 0.3 and 4.5 mg/mL of saccharides.

4. The extract of claim 1, wherein lysis is performed at a pH of 12.6 to 13.4.

5. The extract of claim 1, wherein the extract is treated so as to remove particulate and/or insoluble components or both.

6. The extract of claim 1, wherein the one or more bacterial species is cultured in a medium that does not pose a risk of prion diseases.

7. The extract of claim 1, wherein the extract comprises between 1.5 and 2.5 mg/mL of free amino acids chosen from aspartic acid, glutamic acid, serine, histidine, alanine, arginine, tyrosine, methionine, phenylalanine, and lysine, and wherein at least one of said free amino acid is racemized by at least 10%.

8. The extract of claim 1, wherein the free amino acids in the extract comprise between 1 and 80% D-amino acids.

9. The extract of claim 8, wherein the free amino acids in the extract comprise between 10 and 45% D-amino acids.

10. The extract of claim 9, wherein the free amino acids in the extract comprise between 25 and 35% D-amino acids.

11. The extract of claim 1, wherein the extract comprises less than 1000 ng/ml of LPS equivalents according to a limulus amoebocyte lysate (LAL) chromogenic test.

12. The extract of claim 1, wherein the survival rate of at least 8 mice with wild-type LPS sensitivity 13 days after challenge with *Salmonella thyphimurium* is at least 70% when treated with said extract for a period of 10 days prior to the challenge, wherein the dose of *Salmonella thyphimurium* is chosen such that the survival rate of at least 8 control mice treated with water is 60% or lower.

13. The extract of claim 12, wherein the survival rate of the mice treated with said extract is at least 80%.

14. The extract of claim 13, wherein the survival rate of the mice treated with said extract is at least 90%.

15. A pharmaceutical composition comprising the extract of claim 1.

16. A method of treating, preventing a subject suffering from or at risk of developing a respiratory disorder or allergic condition, comprising administering an effective amount of the extract of claim 1 or the pharmaceutical composition of claim 15 to said subject.

17. The method of claim 16, wherein the subject is a human or domestic mammal.

18. The method of claim 16, wherein the respiratory disorder or allergic condition is chosen from upper and lower respiratory infections, atopic dermatitis, nasopharyngitis, sinusitis, pharyngitis, tonsillitis, laryngitis, tracheitis, laryngopharyngitis, influenza, pneumonia, bronchopneumonia, bronchitis, lower respiratory infections, allergic rhinitis, allergic asthma, rhinitis, nasopharyngitis, pharyngitis, sinusitis, tonsillitis, laryngitis, laryngotracheitis, bronchitis, obstructive pulmonary disease with acute lower respiratory infection, and obstructive pulmonary disease with acute exacerbation.

* * * * *

UNITED STATES PATENT AND TRADEMARK OFFICE
CERTIFICATE OF CORRECTION

| | |
|---|---|
| PATENT NO. | : 8,697,154 B2 |
| APPLICATION NO. | : 12/530130 |
| DATED | : April 15, 2014 |
| INVENTOR(S) | : Bauer et al. |

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1,050 days.

Signed and Sealed this
Eighth Day of December, 2015

Michelle K. Lee
*Director of the United States Patent and Trademark Office*